United States Patent [19]

Fenner et al.

[11] 4,024,332

[45] May 17, 1977

[54] AMINOGLYCOSIDE ANTIBIOTICS AND INTERMEDIATES THEREFOR

[75] Inventors: Brian Richard Fenner, Broadstairs; John David Hardstone, Deal; Michael Ramond Graves Leeming, Canterbury, all of England

[73] Assignee: Pfizer Inc., New York, N.Y.

[22] Filed: June 4, 1974

[21] Appl. No.: 476,269

[30] Foreign Application Priority Data

June 5, 1973 United Kingdom ............. 26718/73
June 5, 1973 United Kingdom ............. 26719/73

[52] U.S. Cl. ................................. 536/10; 424/180; 536/4; 536/12; 536/17
[51] Int. Cl.² ........................................ C07H 15/22
[58] Field of Search ................ 260/210 AB, 210 K; 424/181; 536/10, 17, 12, 4

[56] References Cited

UNITED STATES PATENTS 3,282,783  11/1966  Vanderhaeghe .................. 424/181

OTHER PUBLICATIONS

Kobayashi et al., The Syns of Kanamycin–6''–Uronic Acid, ect., J. of Antibiotics, vol. 23, 1970, pp. 225–230.
Omoto et al., Separation of Amino Gly. Antibiotics by Gas–Liquid Chrom., J. of Antibiotics, vol. 24, 1971, pp. 430–434.

*Primary Examiner*—Johnnie R. Brown
*Attorney, Agent, or Firm*—Connolly and Hutz

[57] ABSTRACT

Certain novel derivatives of naturally-occurring aminoglycoside antibiotics such as neamine, kanamycins A and B, 3',4'-dideoxykanamycin B, 3',4'-dideoxy-4,5-dehydrokanamycin B, tobramycin and the gentamicins $C_2$ and $C_{1a}$. The novel derivatives possess an optionally-substituted homo-or heteroarylmethyl group on the nitrogen atom of the aminomethyl moiety at the C-6' position of the natural aminoglycoside and are useful as antibacterial agents.

26 Claims, No Drawings

AMINOGLYCOSIDE ANTIBIOTICS AND INTERMEDIATES THEREFOR

BACKGROUND OF THE INVENTION

The invention relates to antibacterial agents and intermediates for the preparation thereof, and its particularly concerned with a class of novel antibacterial 2-deoxystreptamine aminoglycosides, with novel intermediates for the preparation thereof; and with methods for the preparation of such aminoglycosides and intermediates.

Naturally-occurring 2-deoxystreptamine aminoglycosides have in common a three-ring structure which may be represented by the general formula:

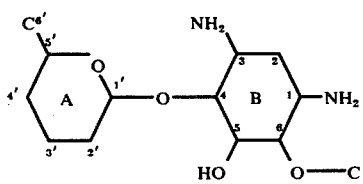

where the ring A is the skeleton of a hexapyranosyl group having an amino group in the 2' - and/or 6' - positions, the ring B is the 2-deoxystreptamine group, and the ring C represents a glycosyl group attached by the glycosidic linkage to the 6-position of the streptamine ring B.

The novel antibacterial agents of the invention are a series of 2-deoxystreptamine aminoglycosides having a substituted amino group in the 6'-position of the hexopyranosyl ring A and preferably having the glycosyl group attached to the 6-position of the streptamine ring B. Such compounds are effective in treating a variety of gram-positive or gram-negative bacterial infections, such as urinary tract infections, in animals, including humans, and possess advantages in use over 2-deoxystreptamine aminoglycosides having an unsubstituted amino group in the 6'-position of the hexopyranosyl ring A, such as the naturally occurring kanamycins A and B, tobramycin, gentamicins $C_{1a}$ and $C_2$, neomycins and ribostamycin, and known transformation products thereof such sisomycin and 3',4'-dideoxykanamycin B.

SUMMARY OF THE INVENTION

It is an object of this invention to provide novel chemical compounds which are of value as antibacterial agents; and the novel chemical compounds to be considered to be within the scope of the invention are those of formula:

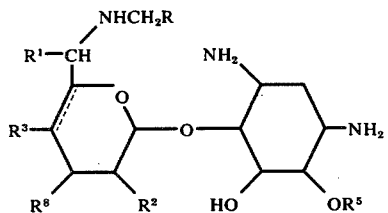

and the pharmaceutically-acceptable acid-addition salts thereof;

Wherein R is an aromatic carbocyclic or heterocyclic group, which can be a mono-, bi- or tricyclic group, and which can be substituted by up to two substituents each selected from the group consisting of fluoro, chloro, bromo, iodo, hydroxy, amino, N-(lower-alkyl)amino, N,N-di(lower-alkyl)amino, lower-alkanoylamino, nitro, lower-alkoxy, lower-alkyl, benzyloxy, trifluoromethyl, carboxy, lower-alkoxycarbonyl and phenyl;

$R^1$ is hydrogen or methyl;
$R^2$ is amino or hydroxy;
$R^3$ and $R^8$ are each hydrogen or hydroxy;
$R^5$ is hydrogen or a glycosyl group;

and the broken line represents an optional second bond between C-4' and C-5';

provided that when the optional second bond is present, $R^3$ and $R^8$ are each hydrogen.

The glycosyl group $R^5$ can be a single pentafuranosyl or hexapyranosyl group, or two or more of such groups joined together by a further glycosidic linkage, as found in naturally-occurring 2-deoxystreptamine aminoglycosides. As well as containing two or more hydroxyl groups, each such group may optionally contain an amino or a methylamino group. Examples of glycosyl groups are those found in kanamycin, gentamicin, ribostamycin, neomycin and lividomycin, (and derivatives thereof), in which glycosyl groups have the following structures, respectively:

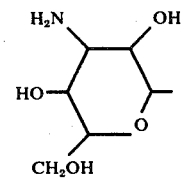

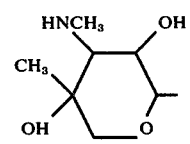

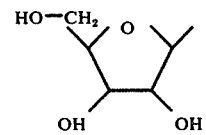

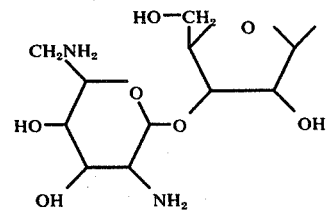

and

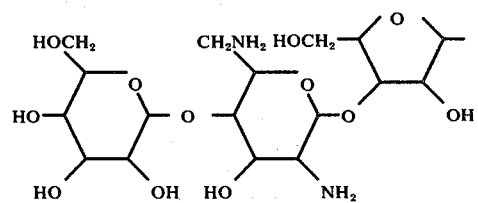

However, a preferred group of antibacterial compounds of this invention is those compounds of formula:

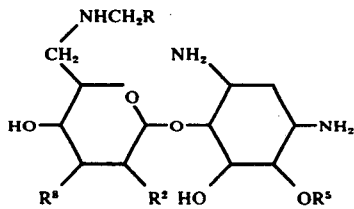

and the pharmaceutically-acceptable acid-addition salts thereof;

wherein R is selected from the group consisting of phenyl, 1- and 2-naphthyl, 1-, 2- and 9-anthryl, 1-,2-,3-,4- and 9-phenanthryl, 2-,3- and 4-pyridyl, 2- and 3-furyl, 2- and 3-thienyl, 2-, 4- and 5-pyrimidyl, 2- and 3-imidazolyl, 2-,3- and 4-quinolyl, 2- and 3-indolyl and

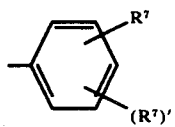

wherein $R^7$ and $(R^7)'$ are each selected from the group consisting of fluoro, chloro, bromo, iodo, hydroxy, amino, N-(lower-alkyl)amino, N,N-di-(lower-alkyl)amino, lower-alkanoylamino, nitro, lower-alkoxy, lower-alkyl, benzyloxy, trifluoromethyl, carboxy, lower-alkoxycarbonyl and phenyl;

$R^2$ is selected from the group consisting of amino and hydroxy;

$R^8$ is selected from the group consisting of hydrogen and hydroxy;

and $R^5$ is selected from the group consisting of hydrogen and

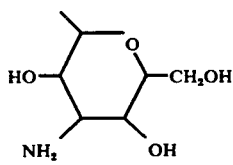

Moreover, within this latter preferred group, particularly desirable compounds are those compounds of formula II, wherein $R^5$ is of formula III and R is selected from the group consisting of phenyl, naphthyl and

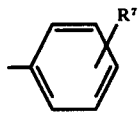

wherein $R^7$ is selected from the group consisting of fluoro, chloro, bromo, iodo, hydroxy, amino, N-(lower-alkyl)amino, N,N-di(lower-alkyl)amino, lower-alkoxy, lower-alkyl and phenyl.

An especially valuable sub-group of antibacterial agents of this invention consists of the compounds of formula II, wherein $R^2$ is amino, $R^5$ is of formula III, $R^8$ is hydroxy, and R is phenyl, naphthyl, 4-biphenylyl, 4-hydroxyphenyl and 4-dimethylaminophenyl.

A further especially valuable sub-group of antibacterial agents of this invention consists of the compounds of formula II, wherein $R^2$ and $R^8$ are each hydroxy, $R^5$ is of formula III, and R is

wherein $R^7$ is selected from the group consisting of hydroxy, amino, N-(lower-alkyl)amino, NN-di(lower-alkyl)amino and lower-alkoxy.

A still further especially valuable sub-group of antibacterial agents of this invention consists of the compounds of formula II, wherein $R^2$ is amino, $R^5$ is of formula III, $R^8$ is hydrogen, and R is phenyl, naphthyl or 4-biphenylyl.

Highly desirable individual compounds of the instant invention are:
6'-N-(4-hydroxybenzyl)kanamycin A
6'-N-(2-hydroxybenzyl)kanamycin A
6'-N-(4-dimethylaminobenzyl)kanamycin A
6'-N-(4-aminobenzyl)kanamycin A
6'-N-benzylkanamycin B
6'-N-1-naphthylmethylkanamycin B
6'-N-2-naphthylmethylkanamycin B
6'-N-4-biphenylylmethylkanamycin B
6'-N-benzyltobramycin
6'-N-(4-hydroxybenzyl)kanamycin B
6'-N-(4-dimethylaminobenzyl)kanamycin B

DETAILED DESCRIPTION OF THE INVENTION

Throughout this specification, "halogen" means fluorine, chlorine, bromine or iodine, and the term "lower" applied to a particular group indicates that such a group possess not more than six carbon atoms. Where a particular group has from 3 to 6 carbon atoms, it may be straight or branched-chain.

The novel compounds of formula I can be prepared by a number of different processes according to the invention. In one process, they are prepared from compounds of the formula:

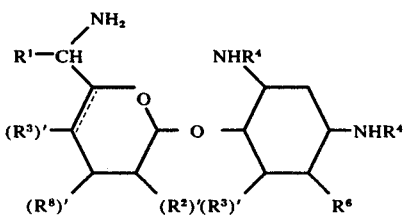

wherein $R^1$ is hydrogen or methyl;
$(R^2)'$ is hydroxy, protected hydroxy or $R^4NH$;
$(R^3)'$ and $(R^8)'$ are each hydrogen, protected hydroxy, or hydroxy;
$R^4$ is a mono-valent protecting group for a primary amino group;
and $R^6$ is hydroxy, protected hydroxy or a group $O-(R^5)'$ in which $(R^5)'$ represents a glycosyl group as previously defined except that any primary amino group therein is replaced by a group $R^4NH$ and any free hydroxy group therein can optionally be protected; by reacting the compound of form IV with an aldehyde of formula R-CHO, subsequently reducing the Schiff's base so formed to the corresponding secondary amine and then removing the groups $R^4$ and de-protecting any remaining protected hydroxy groups.

This process may be represented by the following reaction scheme:-

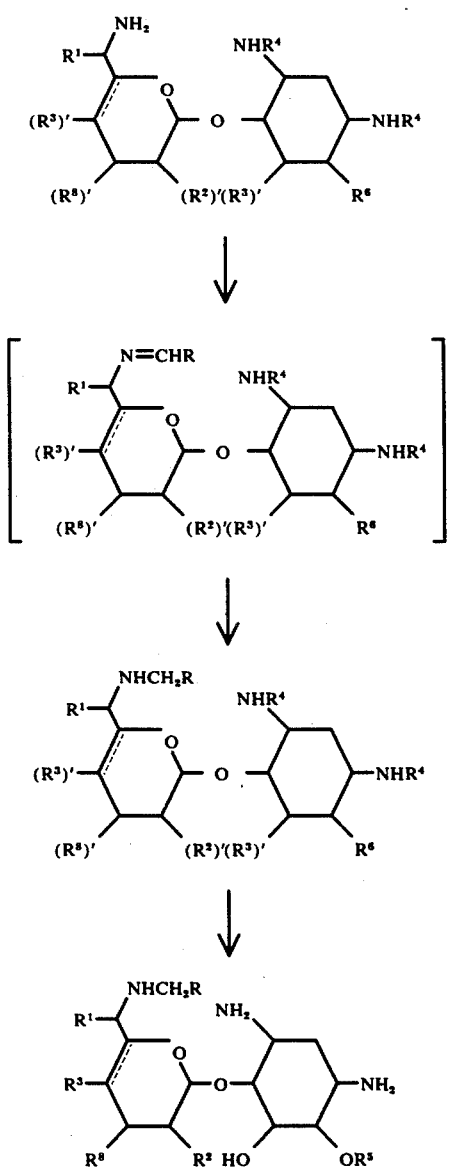

The monovalent protecting group $R^4$ is derived from a reagent selective for primary amino groups and easily removable subsequently by conventional techniques, e.g., hydrolysis. Examples of the group $R^4$ are the formyl, lower-alkanoyl, halo-substituted lower-alkanoyl, aryl(lower-alkanoyl), aroyl, lower-alkoxycarbonyl, halo-substituted lower-alkoxycarbonyl, aryl lower-alkoxycarbonyl and aryloxycarbonyl groups. In this connection, typical examples of "aryl" are phenyl and phenyl substituted with one or more substituents chosen from halo, lower-alkyl, lower-alkoxy and nitro. Specific examples of the group $R^4$ are trifluoroacetyl, methoxycarbonyl, tertiary-butyloxycarbonyl, 2,2,2-trichloroethoxycarbonyl and benzyloxycarbonyl, of which methoxycarbonyl and tertiary butyloxycarbonyl are particularly preferred. The reagents from which the lower-alkoxycarbonyl, aryl lower-alkoxycarbonyl and aryloxycarbonyl groups are derived are generally their halides, more particularly chlorides, whereas the reagents from which the remaining groups, except formyl, are derived are the corresponding acid chlorides or anhydrides. The reagents from which the formyl group may be derived include formic acid and its esters, e.g. ethyl formate. The tertiary-butyloxycarbonyl group may also be derived from its azide (tertiary-butyl azidoformate).

Protecting groups for single hydroxy groups are suitably introduced by reagents which react with alcoholic hydroxy groups and are readily removable by hydrolysis or hydrogenolysis at a subsequent stage and are exemplified by aryl lower-alkyl, formyl, lower-alkanoyl, aryl(lower-alkanoyl), aroyl, lower-alkylsulfonyl, aryl(lower-alkyl)sulfonyl, arylsulfonyl and tetrahydropyranyl. Typical examples of aryl are phenyl and substituted phenyl as previously indicated. Reagents by which aryl(lower-alkyl), lower-alkylsulfonyl, aryl(lower-alkylsulfonyl) and arylsulfonyl groups may be introduced are their halides, especially chlorides.

The reagents by which the lower-alkanoyl, aryl(lower-alkanoyl) and aroyl groups may be introduced are the corresponding acid halides (e.g. chlorides) or anhydrides, and the formyl group may suitably be introduced by a lower-alkyl formate, e.g. ethyl formate. Finally, the tetrahydropyranyl protecting group is suitably introduced by effecting an addition reaction between the hydroxy group and dihydropyran under anhydrous acidic conditions.

Protecting groups for two adjacent hydroxy groups may also be derived from reagents selective for the 1,2-diol system, and easily removable by conventional techniques, e.g. hydrolysis at a subsequent stage. Examples of such divalent protecting groups are methylene, dialkylmethylene (the lower-alkyl groups therein being the same or different), diarylmethylene (same or different aryl groups), cyclopentylidene, cyclohexylidene or cycloheptylidene optionally substituted with one or more lower alkyl groups, and dialkyl silylidene. Specific examples are isopropylidene, cyclohexylidene, 2,2,6,6-tetramethylcyclohexylidene and dimethylsilylidene. A methylene protecting group may suitably be introduced by means of methylene dibromide or diiodide, whereas the dichloride of an appropriate diarylmethane is a suitable source of a diarylmethylene group. Acetone, under acidic conditions, may be used for introduction of an isopropylidene group, while analogous dialkylmethylene groups may be derived from the appropriate dialkyl ketones and introduced under similar conditions. A ketal, e.g., the diethyl ketal, of an optionally substituted cyclopentanone, cyclohexanone or cycloheptanone is the preferred reagent for introduction of an optionally substituted cyclopentylidene, cyclohexylidene or cycloheptylidene group, while a dialkylsilylidene group is suitably introduced using a dialkylsilyl chloride, e.g. dimethysilyl chloride.

This process for the production of the novel compounds of formula I from the compounds of formula IV, according to the present invention, entails, as an initial stage, a conventional Schiff's base formation reaction between a primary amine and an aldehyde, the latter preferably being used in slight excess. Such a reaction may be performed with the reactants dissolved in a reaction-inert organic solvent, e.g. methanol, and at a temperature generally between room temperature and reflux temprature, depending on the nature of the particular reactants and solvent employed. The period within which the reaction goes substantially to completion depends on the nature of the reactants, solvent, and the temperature at which it is performed. The reaction between the compound of the formula IV and the aldehyde R-CHO is generally substantially complete within 24 hours when it is performed in methanol at room temperature and with a slight excess of aldehyde over amine.

The second stage, involving the reduction of the Schiff's base of formula V, formed in the initial stage, is suitably effected using sodium borohydride as the reducing agent and can be conveniently performed by adding the latter to the reaction mixture of the first stage, thereby avoiding the necessity to isolate the Schiff's base product as a preliminary step. The reduction has been found to go substantially to completion within 24 hours when the reaction is performed at room temperature, and the secondary amine product is conveniently isolated by neutralising the reaction mixture, e.g. by adding a sufficient quantity of a dilute mineral acid such as hydrochloric acid, evaporating it in vacuo to dryness, extracting the resulting residue with a suitable organic solvent, e.g. chloroform, optionally washing the organic solvent with water, and evaporating the organic solution of the product in vacuo to dryness, thereby affording the secondary amine product in a crude state. If desired, the product may be recrystallised from a suitable solvent to a higher degree of purity prior to the final stage of the process.

Alternatively, the first two stages may suitably be carried out effectively in a single stage by submitting a mixture of the starting primary amine and aldehyde, dissolved in a suitable solvent, e.g. ethanol, to a conventional catalytic hydrogenation.

The final stage of this process for the production of compounds of formula (I) according to the invention, involves the removal by conventional means of the protecting groups $R^4$ from the amino groups and any protecting groups from protected hydroxy groups present in the compound of the formula VI. There are various conditions for completely removing protecting groups from amino or hydroxy groups, which depend on the nature of the particular protecting groups and the environment of the protected amine or hydroxy groups. The medium employed may be anhydrous or aqueous, and in particular instances it may be acidic or basic to various strengths. The procedure may involve more than one step, for example in cases where the amine-protecting groups are removable under basic conditions and hydroxy-protecting groups under acidic conditions, or vice versa, or where both the amino- and hydroxy-protecting groups are removable under acidic or basic conditions but in different acidic or basic media, respectively. Conditions which can be used in any particular case will be obvious to one skilled in the art.

A particularly preferred protecting group $R^4$ for the amino groups is the methoxycarbonyl group. This group may be removed in a medium comprising aqueous barium hydroxide solution, containing a large excess of barium hydroxide with respect to the amount of starting material present, if the mixture is heated at 90° C. over several hours, e.g. during an overnight period. Thereafter, the barium ions are conviently removed from solution by precipitation, as in the form of barium carbonate (using the passage of carbon dioxide through the solution to promote the deposition) and filtration, the aqueous solution (in the case where there are no hydroxyl-protecting groups to be removed) then being evaporated to dryness, e.g., in vacuo, to afford the required final product. The latter may then be recrystallised to purify from a suitable solvent and/or converted into an acid-addition salt by conventional means, the salt then, if necessary, being recrystallised to purify from a suitable solvent.

In the case where acid-labile hydroxyl-protecting groups remain to be removed from the compound after removal of the amino-protecting groups $R^4$, the aqueous reaction solution, with the barium ions removed therefrom, is acidified by addition of a sufficient quantity of acid, e.g., hydrochloric acid. The acidic solution is then heated, e.g., over a steam bath, for a sufficient period of time, e.g., 2 hours, for the hydroxy-protecting groups to be removed. Thereafter the product is conveniently isolated by neutralising the reaction solution, e.g., by addition of aqueous sodium bicarbonate solution, evaporating the solution to dryness, extracting the solid residue with a suitable organic solvent, e.g., methanol, and evaporating the resulting organic solution to dryness. The crude product may then be purified, e.g., by recrystallisation from a suitable solvent or by a conventional column chromatographic technique. Conversion into an acid-addition salt may be effected by conventional means if desired.

Another preferred protecting group $R^4$ for the amino groups is the tertiary butyloxycarbonyl group, which is acid-labile. Such a group may be removed under conditions similar to those described above for the removal of the cyclohexylidene group, and the total deprotection process involving removal of both such protecting groups may therefore be achieved in a single stage with a suitable choice of conditions.

When it is desired to prepare by the process of the invention compounds of the formula (I) in which R represents an aromatic group substituted with lower-alkoxycarbonyl, an additional esterification stage may be required if the lower alkoxycarbonyl group has been hydrolysed to a carboxy group in the final deprotection stage of the main process. The additional stage comprises esterifying the product with an appropriate lower-alkanol, by conventional means. Alternatively, the aldehyde starting material, R-CHO, may be a carboxy-substituted aromatic aldehyde and the carboxylic acid group is esterified to yield the required lower-alkoxycarbonyl compound in the additional esterification stage.

Naturally, if it is desired to prepare compounds of the formula (I) in which R represents an carboxy-substituted aromatic group and the conditions of the final stage of the main process are such as to hydrolyse lower-alkoxycarbonyl groups to carboxy groups, then the starting aldehyde, R-CHO, may contain a lower alkoxycarbonyl substituent which is then hydrolysed to a carboxylic acid group in that final stage.

Similarly, when it is desired to prepare compounds of the formula I, wherein R is substituted with an amino group, the starting aldehyde R-CHO may contain a nitro or lower-alkanoylamino group, which is subsequently reduced, e.g. using hydrogen in the presence of a Raney nickel catalyst, or hydrolysed, respectively, to yield an amino-substituted product.

The compounds of formula IV are themselves novel compounds. According to the invention they can be prepared by two different methods.

In one method according to the invention they are prepared from compounds of the formula:

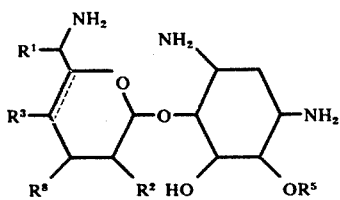

VII wherein $R^1$, $R^2$, $R^3$, $R^5$ and $R^8$ are as previously defined, by first protecting all primary amino groups with the mono-valent protecting group $R^4$, and, if necessary, some or all of the free hydroxyl groups therein, and then selectively deprotecting the 6'-amino group to remove the group $R^4$ therefrom. This process is represented by the reaction scheme:-

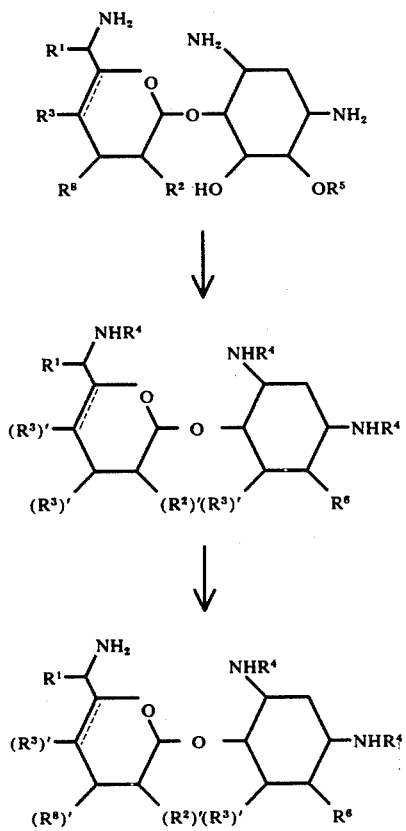

Compounds of the formula VII in which $R^5$ is hydrogen are known degradation products of naturally-occurring aminoglycoside antibiotics, such as neamine and 3',4'-dideoxyneamine, while those in which $R^5$ is a glycosyl group are known aminoglycoside antibiotics such as kanamycin A and B, gentamicin $C_{1a}$ and $C_2$, tobramycin, neomycin and ribostamycin, or known transformation products thereof such as sisomycin and 3',4'-dideoxykanamycin B.

We have discovered that the protecting group $R^4$ can be selectively removed from the amino group attached to the 6'-carbon atom by controlled solvolysis. According to another aspect of the invention, therefore, a process for preparing a compound of the formula Iv comprises solvolysing a compound of the formula VIII under conditions such that only one of the groups $R^4$ is removed therefrom.

There are various conditions of solvolysis utilisable for removing protecting groups from amino groups, which depend on the nature of the particular protecting group and the environment of the protected amino group. As in the case of the removal of protecting groups from compounds of the formula (IV), the medium employed for such deprotection reactions may be anhydrous or aqueous, and in particular instances it may be acidic or basic to various stengths. The controlled solvolysis process of the present invention is effectively performed by using milder conditions than would be used if it were desired to remove all the amino-protecting groups $R^4$ from a compound of the formula IV, for example by employing (1) a reaction medium of lower acid or base strength, (2) a smaller proportion of acid or base to protected compound, (3) a shorter reaction time, (4) a lower reaction temperature, or (5) a combination of any of these conditions to produce overall milder reaction conditions. We have discovered that, as an initial stage, the fully protected compound in the solvolytic environment loses only one of its protecting groups, that of the C-6'amino group, this process becoming substantially complete before the remaining amino-protecting groups $R^4$ are removed.

Hence this aspect of the invention resides in the choice of conditions such that the reaction is terminated at the stage when the mono-deprotection process is substantially complete.

The process according to this aspect of the invention has been found to be particularly effective when $R^4$ represents a methoxycarbonyl group, if it is carried out within a temperature range of from about 10° to about 50° C., using aqueous barium hydroxide solution as the solvolytic medium, progress of the reaction being followed by thin-layer electrophoresis or thin-layer chromatography. Preferably the aqueous barium hydroxide solution is employed in such quantity that the molar proportion of barium hydroxide to the compound of the formula VIII is about two to one, and at a strength of approximately 1.6N, under which conditions the desired mono-deprotection process is substantially complete after ca. 24 hours at 20° C. or ca. 3 hours at 40° C. At the stage of substantial completion of mono-deprotection, the barium ions are conveniently removed from solution by precipitation, as previously described, in the form of barium carbonate, and filtration, the aqueous solution then being evaporated to dryness to afford the required mono-deprotected product of the formula IV.

The process according to this aspect of the invention has also been found to be particularly effective when $R^4$ represents a tertiary-butyloxycarbonyl group, if it is carried out at room temperature using aqueous acetic acid as the solvolytic medium, progress of the reaction again being followed by thin-layer electrophoresis or thin-layer chromatography. Preferably, the aqueous acetic acid is a 50% aqueous solution and the amount of acid used constitutes a large molar excess in relation to the compound of the formula VIII, under which conditions the desired mono-deprotection process is substantially complete after about 5 days at about 20° C. At this stage, the mono-deprotected compound of the formula IV is conveniently isolated by removing any unchanged starting material by extraction in an organic solvent, e.g., chloroform, basifying the aqueous solution, e.g., by addition of aqueous sodium bicarbonate solution, extracting the basified bicarbonate solution, extracting the basified solution with an organic solvent, e.g., chloroform, and evaporating the organic solution to dryness, thereby yielding the solid product.

In the second method according to the invention for preparing compounds of formula IV, they are prepared from compounds of formula VII by first selectively protecting the 6' - amino group with a benzyloxycarbonyl group, then protecting the remaining primary amino groups with a mono-valent protecting group $R^4$ (other than a benzyloxycarbonyl group) and finally selectively removing the benzyloxycarbonyl group.

This process is represented by the reaction scheme:

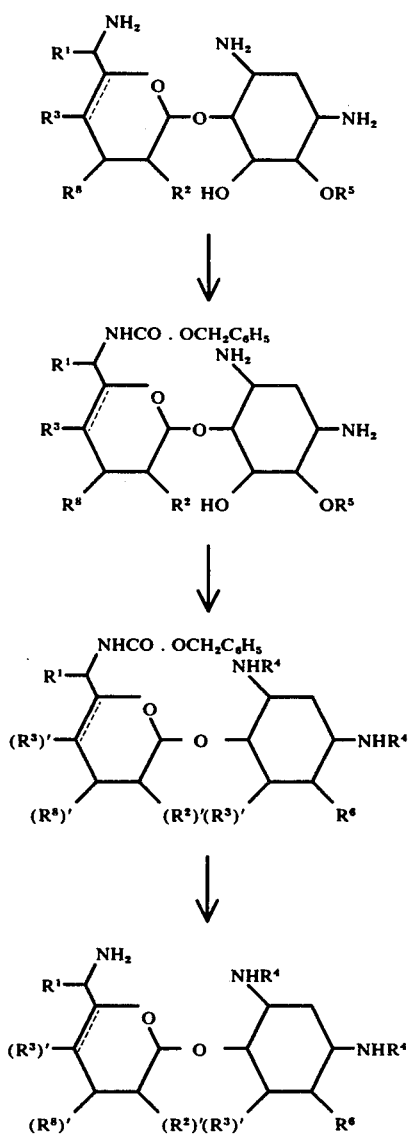

Compounds of formula IX in which the 6' - amino group is selectively protected with a benzyloxycarbonyl group are known compounds, and their preparation is described, for example, in Netherlands Pat. Application No. 7209617 (Belgian Pat. No. 786201), West German Pat. Application No. 2311524 and "Journal of Antibiotics," 25, 695 (1972).

The benzyloxycarbonyl group may be selectively removed from the 6' - amino group by hydrogenolysis, e.g., by hydrogenation in aqueous acidic solution in the presence of a palladium-on-carbon catalyst at moderate temperatures and pressures e.g. at about 30° C under a pressure of about 50 psi. Hydrogenolysis is normally complete under these conditions in less than 12 hours. The product may then be recovered by neutralising the hydrogenated reaction mixture with aqueous ammonia and evaporation to dryness.

Alternatively, the benzyloxycarbonyl group may be selectively removed by treatment with sodium in anhydrous liquid ammonia at the reflux temperature of the solvent. After conversion of excess sodium to chloride by addition of ammonium chloride, the product may then be recovered by suspension in water, neutralisation with aqueous hydrochloric acid and filtration of the solid precipitate.

The novel intermediates of the formula IV may exist in various conformational forms, and this invention is not limited to any one such form thereof. Generally, the rings A and B are each in the 'chair' form, and each of the groups $(R^2)'$, $(R^3)'$, $NHR^4$ and $R^6$, and the 6' - $R^1CH(NH_2)$ group, are disposed either axially or equatorially with respect to the rings A and B. Furthermore, the glycosidic linkage between the hexopyranosyl ring A and the 2-deoxystreptamine ring B is more usually an α-linkage with respect to the former, particularly when the compounds of the formula VII from which they are derived are obtained from naturally-occurring 2-deoxystreptamine aminoglycosides.

The novel compounds of formula I can also be prepared directly from compounds of the formulae VII by several different methods according to the invention.

In one method, compounds of formula VII may be reacted with an aldehyde of the formula R-CHO and reduced to form compounds of the formula I directly, the reaction conditions being as described in the preparation of the protected compounds of formula VI from the mono-deprotected compounds of formula IV. This method is based on the discovery that the aldehyde R-CHO reacts selectively with the 6'- amino group of compounds of formula VII.

In another method according to the invention, compounds of formula VII and IV may be reacted with a halide of the formula $R-CH_2X$, where X is halo, preferably chloro, to form compounds of formulae (I) and VI, respectively, the latter being subsequently treated to remove the protecting groups $R^4$ (and to de-protect any protected hydroxy groups) to yield compounds of formula (I) as previously described. As a further variation of this process, according to the invention, compounds of formula VII and IV can be reacted with an acylating agent of the formula R-CO-X, where X is halo preferably chloro, or any other suitably reactive acylating agent derived from the acid R-COOH, e.g., the succinimido ester of the acid, to form compounds of the formulae:

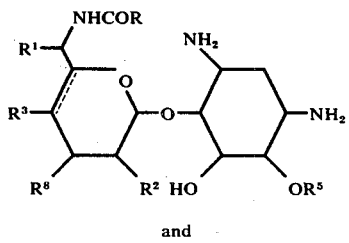

and

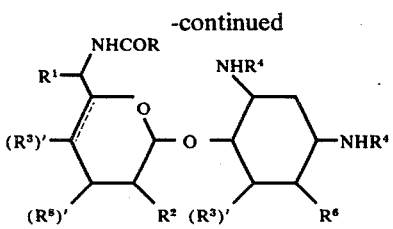

respectively.

The compounds of formulae XI and XII are then reduced by conventional means, e.g., by diborane, to compounds of formulae I and VI, respectively, those of formulae VI then being converted to compounds of formula I as before. This method, and its variation, when applied to compounds of formula VII is based on the discovery that the compounds of formulae R-CH₂X and R-CO-X react selectively with the 6'- amino group of compounds of formula VII.

In each of the methods just described, when an aldehyde R-CHO, or a compound of the formula R-CH₂-X or R-CO-X, is reacted with a compound of formula VII, it should preferably be used in approximately equimolar proportions with the compounds of formula VII, since any significant excess will result in compounds being formed which contain RCH₂- groups attached to other amino groups in the molecule. If only a moderate excess is used, however, (e.g. less than twice molar) then the desired product may relatively easily be separated from minor amounts of compounds containing more than one group RCH₂-, e.g. by chromatographic methods.

The compounds of formula I according to the invention, like those of formula IV, may exist in various conformational forms, and the invention is not limited to any one such form thereof. Generally the rings A and B are each in the "chair" form, and each of the moieties CH(R¹)NHCH₂R,R², R³ (if other than a hydrogen) and OR⁵, as hereinbefore defined, and the amino and hydroxy groups, is disposed either axially or equatorially with respect to the rings A and B. Furthermore, the glycosidic linkage between the hexopyranosyl ring A and the 2-deoxystreptamine ring B is more usually an α-linkage with respect to the former, particularly when the compounds of the formulae IV or VII, the precursors to those of the formula I, are obtained from naturally-occurring 2-dexoystreptamine aminoglycosides.

A characteristic feature of the compounds of this invention is their ability to form acid-addition salts, and all such salts are to be considered within the scope and purview of this invention. Although when contemplating therapeutic use of a compound of this invention, it is advisable to use a pharmaceutically-acceptable salt, other salts can be used for a variety of other purposes, such as, for example, isolating and purifying individual compounds of the invention, and interconverting pharmaceutically-acceptable acid-addition salts with their non-salt counterparts. Pharmaceutically-acceptable acid-addition salts of the compounds of the invention are those formed from acids which form non-toxic acid-addition salts, containing pharmaceutically-acceptable anions, such as the hydrochloride, hydrobromide, hydroiodide, sulfate or bisulfate, phosphate or acid phosphate, acetate, maleate, fumarate, oxalate, lactate, tartrate, citrate, gluconate, saccharate and p-toluenesulfonate salts.

The in vitro activity of the antibacterial compounds of the instant invention can be demonstrated by the conventional two-fold serial dilution technique in Brain-Heart Infusion broth (Difco). The broth is inoculated with bacteria, and with the test antibiotic, and then it is incubated for 24 hours at 37° C. At this point, the test is read visually. The minimum inhibitory concentration (MIC) of test compound is the lowest concentration which prevents turbidity, i.e., which prevents growth of the bacteria. Typical bacteria which have been used in these tests are strains of *Escherichia coli, Klebsiella pneumoniae, Proteus mirabilis, Pseudomonas aeruginosa, Staphylococcus aureus* and *Staphylococcus faecalis*. In vitro activities of a number of the compounds of the invention are shown later in this specification.

In vivo evaluation of the compounds has also been carried out for the more active compounds, by administering the compounds subcutaneously to groups of mice which have been infected by a lethal dose of *Escherichia coli*. Each compound is administered at a series of dosage levels, and activity is expressed as the dosage level of antibiotic which produces a 50% survival rate of the infected mice, over a 72 hour period.

For human use, the antibacterial compounds of the invention can be administered alone, but will generally be administered in admixture with a pharmaceutical carrier selected with regard to the intended route of administration and standard pharamceutical practice. For example, they may be administered orally in the form of tablets containing such excipients as starch or lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to human patients it is expected that the daily dosage level of the antibacterial compounds of the invention will be comparable with that of aminoglycoside antibacterial agents currently in use, e.g., from 0.1 to 50 mg/kg (in divided doses) when administered by the parenteral routes, or from 10 to 100 mg/kg (in divided doses) when administered by the oral route. Thus tablets or capsules of the compounds can be expected to contain from 0.1 to 1 g of active compound for administration orally up to 4 times a day, while dosage units for parenteral administration will contain from 10 to 500 mg. of active compound. The physician in any event will determine the actual dosage which will be most suitable for an individual patient and it will vary with age, the weight and response of the particular patient. The above dosages are exemplary of the average host. There can, of course, be individual cases where higher or lower dosage ranges are merited, and such are within the scope of this invention.

The invention is exemplified by, but not limited by, the following Examples.

EXAMPLE I 5,6-O-Cyclohexylidene-2',1,3-tri(N-carbomethoxy)-neamine

A. To a solution of neamine (16.1 g, 0.05M) and sodium carbonate (15.9 g., 0.15M) in water (150 ml), cooled by an ice-bath, was added dropwise with stirring a solution of methyl chloroformate (23.6 g., 0.25M) in acetone (150 ml). The solution was stirred for 3 hours, and then allowed to stand overnight at room temperature, the resulting white precipitate then being collected by filtration, washed with water followed by acetone and dried in vacuo at room temperature to afford 25.0 g of tetra(N-carbomethoxy)neamine, m.p. 300° C., representing 90% of the theoretical yield.

Analysis: Required for $C_{20}H_{34}N_4O_{14}$; C, 43.3; H, 6.2; N, 10.1% Found: C, 42.1; H, 6.05; N, 10.05%.

B. A mixture of tetra(N-carbomethoxy)neamine (5.54 g., 0.01M; prepared as in [A]), cyclohexanone dimethylketal (7.20 g, 0.05M) and p-toluene sulfonic acid (approximately 50 mg) in dimethylformamide (approximately 500 ml) at 50° C was stirred under a pressure of 20 mm of mercury for 1.5 hours and then at atmospheric pressure overnight. Methanol (20 ml) was added, and the solution was stirred for a further 40 minutes.

The reaction solution was then evaporated in vacuo to a gummy residue, which was triturated in chloroform, the gelatinous solid separating then being collected by filtration and washed with chloroform. The chloroform solution and washings were combined, washed with sodium bicarbonate solution, dried over anhydrous magnesium sulphate and the solvent was removed by evaporation in vacuo. Produced was 4.0 g of 5,6-O-cyclohexylidene-tetra(N-carbomethoxy)-neamine. representing 63% of the theoretical yield.

Analysis: Required for $C_{26}H_{42}N_4O_{14}$: C, 49.2; H, 6.65; N, 8.85% Found: C, 49.4; H, 6.95; N, 8.6%.

C. A solution of 5,6-O-cyclohexylidene-tetra(N-carbomethoxy)neamine (10 g, prepared as in (A) but on a larger scale) in a mixture of 4N aqueous barium hydroxide solution (70 ml) and 50% aqueous methanol (300 ml) was stirred at room temperature over a period of 24 hours, during which time samples of the solution were removed periodically and investigated using standard thin layer electrophoretic and chromatographic techniques by comparison with the starting material and neamine. The results indicated that the solution after 24 hours still contained mainly the fully amino-protected starting material.

The methanol present in the solution was substantially removed by partial evaporation in vacuo of the reaction solution, and the aqueous solution was stirred at room temperature for a further 24 hours at the end of which period tin layer electrophoretic and chromatographic evidence indicated that the deprotection process had afforded substantially a single product unaccompanied by a significant quantity of unchanged starting material.

A stream of carbon dioxide as then passed through the reaction solution until the latter was at pH 7, and the resulting precipitate of barium carbonate and other solid matter was removed by filtration. Evaporation of the filtrate in vacuo to dryness afforded 11.0 g of 5,6-O-cyclohexylidene-2',1,3-tri(N-carbomethoxy)neamine in a damp state.

CHARACTERIZATION OF PRODUCT

A sample of the product was converted, through Schiff's base formation with benzaldehyde, and subsequent reduction with sodium borohydride, to the appropriate N-benzyl derivative of the primary amine product of the aforedescribed experimental procedure. The remaining, protected, amino groups were then deprotected by hydrolysis in aqueous barium hydroxide solution, at 90° C., all of which processes are described in more detail in Example 11, hereafter.

EXAMPLE 2

5,6-O-Cyclohexylidene-2',1,3-tri(N-carbomethoxy)-neamine

A solution of 5,6-O-cyclohexylidene-tetra(N-carbomethoxy)neamine (10 g) in a mixture of 4N aqueous barium hydroxide solution (100 me) and 50% aqueous methanol (300 ml) was stirred at room temperature for 2 hours, after which it was partially evaporated in vacuo at approximately 40° C. for removal of methanol. Water was added to bring the volume of the solution to about 300 ml, and the aqueous solution was stirred at room temperature for a further 48 hours, at the end of which period thin layer electrophoretic and chromatographic evidence indicated that the deprotection process had afforded substantially a single product unaccompanied by a significant quantity of unchanged starting material.

The reaction solution was filtered to remove a fine suspension of solid which had formed during the stirring period, and a stream of carbon dioxide as then passed through the filtrate until the latter was at pH 7, the resulting precipitate of barium carbonate and other solid matter subsequently being removed by filtration. After washing the filtrate with chloroform to remove traces of unchanged starting material possibly present, the aqueous solution was evaporated in vacuo to a small volume, filtered once again, and evaporated in vacuo to dryness. The residue was taken up in turn into two quantities of dry methanol and two of dry benzene and the solutions evaporated to dryness, affording, upon the final evaporation, 9.6 g. of 5,6-O-cyclohexylidene-2'-1,3-tri(N-carbomethoxy)neamine, the same product as produced in Example 1. The latter product was then acylated, using acetic anhydride in methanol, at the four amino groups (at least one being secondary, the remaining being primary) present in the molecule, and the cyclohexylidene protecting group was removed, under acidic hydrolytic conditions, from the 5,6-diol grouping. Finally the four free hydroxyl groups were converted into trimethylsilyloxy groups by reaction with trimethylsilyl chloride, and the product was submitted to a mass spectroscopic investigation, from which it was concluded that the deprotection process had resulted in the removal of a single methoxycarbonyl group from one of the two protected amino groups in the ring A of the fully amino-protected starting material.

EXAMPLE 3

5,6O-Cyclohexylidene-2',1,3-tri(N-carbomethoxy)-neamine

The procedure of the Example 2 was repeated on a larger scale and the characteristic properties of the product were found to be as follows:

Melting point: 160–173° C with decomposition, Infra-red spectrum(KRr disc): Major bands at 3300, 2950, 1720, 1700, 1530, 1280, 1270, 1060 and 1050 $cm^{-1}$ Thin layer electrophoresis: $R_f = 0.2$ (The electrolyte was an equipart mixture of acetic and formic acds, giving a pH value of 2 and a potential difference of 900 volts for 45 minutes was applied across the ends of the silica plate. Detection was performed by drying the plate, spraying with a cyclohexane solution of tertiary-butyl hypochlorite and then drying, cooling and developing the plate with starch-potassium iodide solution. Under these conditions the reference standard neamine gave an $R_f$ value of 0.85).

Nuclear magnetic resonance spectrum, deuterated pyridine:
Major peaks at τ6.24 (singlet, 3H of —$CO_2CH_3$)
  τ6.28 (singlet, 3H of —$CO_2CH_3$)
  τ6.42 (singlet, 3H of —$CO_2CH_3$)
  τ8.3 – 8.7 (multiplet, protons of cyclohexylidene)
Optical Rotation, $[\alpha]_x^{25}$ (C 1.0, $H_2O$):
  X=589, α= + 55.1°
  x=578, α= + 57.6°
  x=546, α= + 65.5°
  x=436, α= +110.3°
  x=365, α= +170.8°
Analysis: Found: C, 51.15; H, 6.97; N, 8.54%, Required for $C_{24}H_{40}N_4O_{12}$: C, 49.99; H, 6.99; N, 9.72%.

EXAMPLE 4

5,6,-O-Cyclohexylidene-2′,1,3-tri(N-carbomethoxy)-neamine

A heterogeneous mixture of 5,6-O-cyclohexylidene-tetra-(N-carbomethoxy)neamine (1.0 g), 4N aqueous barium hydroxide solution (7 ml) and water (15 ml) was stirred at room temperature overnight, after which a stream of carbon dioxide was passed through the mixture until the solution was at pH 7, the resulting precipitate of barium carbonate and other solid matter then being removed by filtration. Evaporation of the filtrate in vacuo afforded an amorphous solid (0.5 g), shown by thin layer electrophoretic and chromatographic evidence to consist substantially of a single product, which was identified as 5,6-O-cyclohexylidene-2′,1,3-tri(N-carbomethoxy)-neamine, the same product as produced in Examples 1, 2 and 3.

CHARACTERIZATION OF PRODUCT

To a stirred solution of the product (50 mg) in dry methanol (10 ml) was added acetic anhydride (0.1 ml) and the resulting solution was then allowed to stand at room temperature for 15 minutes. The solution was evaporated in vacuo to dryness and the residue was triturated in diethyl ether for the purpose of extracting unreacted acetic anhydride. After collecting the solid by filtration, it was crystallised from a mixture of ethyl acetate and n-hexane.

The product, having been shown by thin layer chromatographic evidence to comprise predominantly a single constituent, was then submitted to a melting point determination, elemental analysis and nuclear magnetic resource spectroscopy, the results being as follows:

Melting Point: 160°–170° C with decomposition,
Anaylis: Found: C, 48.90; H, 6.65; N, 8.76%, Required for $C_{26}H_{42}N_4O_{13}$: C, 50.47; H, 6.84; N, 9.05%, (mono-acetylated compound).

Nuclear magnetic resonance spectrum, deuterated pyridine;
Major peaks at
  τ6.25 (singlet, 3H of — $CO_2CH_3$)
  τ6.30 (singlet, 3H of — $CO_2CH_3$)
  τ6.40 (singlet, 3H of — $CO_2CH_3$)
  τ7.98 (singlet, 3H of —$COCH_3$)
  τ8.2–8.6 (multiplet, protons of cyclohexylidene)

It was concluded that only one of the four amino groups in the molecule had been acylated by this procedure, and that the attempted mono-deprotection process described in the example had indeed resulted in the loss of only one of the carbomethoxy protecting groups from the four protected amino groups originally present in the molecule.

EXAMPLE 5

5,6-O-Cyclohexylidene-2′,1,3-tri(N-tertiary-butyloxycarbonyl)neamine

A. A mixture of neamine (32.2 g), tertiary-butyl azidoformate (79.6 g) and finely powdered magnesium oxide (32.0 g) in peroxide-free dioxan (400 ml) and water (200 ml) was stirred at 55° C for 24 hours, after which a further quantity of tertiary-butyl azidoformate (39.8 g) was added and the reaction was allowed to proceed for a further period at 60° C. Water (1 liter) was then added to the reaction mixture, and the solid therefrom was collected by filtration. The solid was triturated in chloroform (4 × 300 ml) and the organic solutions were combined, dried over anhydrous magnesium sulfate and concentrated by evaporation in vacuo to dryness, the residue then being crystallised from aqueous ethanol to afford 19.2 g of tetra(N-tertiary-butyloxycarbonyl)neamine, m.p. 222°–224° C.

B. A solution of the product of (A) (18.2 g) and cyclohexanone dimethyl ketal (28.9 g) in dry dimethylformamide (250 ml) was heated at 50° C and the course of the reaction followed by periodically investigating samples from the reaction solution by thin layer chromatography. After a certain period of incomplete reaction, a quantity of dry p-toluene sulfonic acid was added to bring the pH of the reaction solution to 4, and the reaction mixture was maintained at 50° C for a further 2 hours.

To the cooled reaction solution was added sufficient saturated potassium bicarbonate solution to bring the solution to above pH 7, after which the solution was evaporated in vacuo to dryness. The residue was triturated in chloroform, the insoluble material was removed by filtration, and the filtrate was washed with water and then dried over anhydrous magnesium sulfate. Evaporation of the dry chloroform solution in vacuo yielded a gum (31.6 g) which was then redissolved in chloroform and the solution was passed down a silica gel (Mallinckrodt CC7) column. Elution was performed using a chloroform ethanol gradient to 10% ethanol in chloroform, and two fractions collected yielded, on evaporation to dryness in vacuo, first 1.5 g of 5,6O-cyclohexylidene-tetra(N-tertiary-butyloxycarbonyl)neamine, m.p. 229°–231° C and then 4.22 g of 3′, 4′:5,6-di-O-cyclohexylidene-tetra(N-tertiary-butyloxycarbonyl)-neamine, m.p. 129°–130° C.

Analysis: Found: C, 57.06; H, 8,44; N, 7.25%, Required for $C_{38}H_{66}N_4O_{14}$ (mono-O-cyclohexylidene compound): C, 56.85; H, 8.28; N, 6.98%, Found: C, 59.81; H, 8.20; N, 6120%, Required for $C_{44}H_{74}N_4O_{14}$ (di-O-cyclohexylidene compound): C, 59.85; H, 8.45; N, 6.34%.

C. A heterogeneous mixture of the mono-cyclohexylidene product of (B) (0.262 g) and 50% aqueous acetic acid (15 ml) was stirred at room temperature for 5 days. The resulting homogeneous solution was extracted with chloroform to remove any unreacted starting material, and the aqueous solution was neutralised by addition of aqueous sodium carbonate solution and extracted with chloroform.

The chloroform solution, on being evaporated to dryness in vacuo, afforded a solid (0.056 g), which was shown by thin layer electrophoretic and chromatographic evidence to consist substantially of a single product, identified as 5,6-O-cyclohexylidene-2',1,3-tri(N-tertiary-butyloxycarbonyl)neamine with the following characterising features:

Melting point: 262°–265° C. with decompositions.
Infra-red spectrum, KBr disc: Main bands at 3350, 1680, 1570, 1520 and 1165 cm$^{-1}$.
Nuclear magnetic resonance spectrum: Deuterated pyridine:
Main peaks at
$\tau$8.50 (singlet, 9H of —$CO_2C(CH_3)_3$)
$\tau$8.60 (two singlets, 18H of 2 × $CO_2C(CH_3)_3$)
Thin layer electrophoresis: Rf = 0.1
(The conditions for this were as described under this heading in Example 3).

EXAMPLE 6

3'',2', 1,3-Tetra(N-carbomethoxy)kanamycin B

A homogeneous mixture of kanamycin B (0.042 g), sodium carbonate (0.1 g), methyl chloroformate (0.104 g) and water (3 ml) was stirred at room temperature for 48 hours. The resulting mixture was evaporated to dryness in vacuo, and the residue was triturated in dry methanol. Evaporation of the methanolic solution in vacuo afforded a solid, which was shown by thin layer chromatographic evidence to consist substantially of a single product, identified as penta(-N-carbomethoxy)kanamycin B, with the following characterising features:

Thin layer chromatography, silica:
Product of (A) $R_f$ = 0.90 (Solvent system was an equipart
Cf. kanamycin B $R_f$ = 0.45 mixture of chloroform and 0.880 ammonia)
Product of (A) $R_f$ = 0.6 (Solvent system was an equipart
Cf. kanamycin B $R_f$ = 0.0 mixture of chloroform and methanol)
Nuclear magnetic resonance spectrum, deuterated pyridine: Main peaks at $\tau$6.1, 6.3, 6.4, 6.5 and 6.58 (in each case a singlet, being assigned to 3H of —$CO_2CH_3$)

B. An aqueous solution of the product of (A) and 4N barium hydroxide solution (4.5 ml) (total volume 6.0 ml) was stirred at room temperature for 24 hours, after which a stream of carbon dioxide was passed through the reaction solution until the latter was at pH 7. The resulting precipitate of barium carbonate and other solid matter was removed by filtration, and the filtrate was evaporated to dryness in vacuo to a solid. Thin layer chromatographic and electrophoretic evidence indicated that the product consisted substantially of a single constituent, which was identified as 3'',2',1,3-tetra(N-carbomethoxy)kanamycin B, with the following characterising features:

Thin layer electrophoresis: $R_f$ = 0.30
(The conditions for this were as described under this heading in Example 3. Under such conditions, the reference standard kanamycin B gave an $R_f$ value of 0.65).

EXAMPLE 6A

3'',2'1,3-Tetra(N-carbomethoxy)tobramycin

The procedure of Example 6 is repeated, except that the kanamycin B used therein is replaced by an equimolar amount of tobramycin, to produce the title compound.

EXAMPLE 7

1,3,3''-Tri(N-carbomethoxy)kanamycin A

A. To a cooled solution of kanamycin A sulfate (2.63 g) and anhydrous sodium carbonate (1.57 g) in water (50 ml) was added dropwise a solution of methyl chloroformate (2.84 g) in acetone (50 ml). The mixture was stirred at room temperature for 48 hours, after which the resulting white precipitate was collected by filtration, washed with acetone, and dried in vacuo, affording a solid (1.1 g). Thin layer chromatographic and electrophoretic evidence indicated that the solid consisted substantially of a single product, identified as tetra(N-carbomethoxy)kanamycin A, with the following characterising features:

Thin layer chromatrography, silica:
Product of (A) $R_f$ = 0.70 (Solvent system was an equipart
Cf. kanamycin A mixture of methanol and 0.880
sulfate $R_f$ = 0.46 ammonia)
Thin layer electrophoresis:
Product of (A) $R_f$ = 0.10 (main) 0.37 (trace)
Cf. kanamycin A
sulfate $R_f$ = 0.66
(The conditions for this were as described under this heading in Example 3.)
Analysis: Found: C, 42.72; H, 6.08; N, 7.66%, Required for $C_{26}H_{44}N_4O_{19}$: C, 42.58; H, 6.19; N, 7.82%.

B. The product of (A) (1.1 g), together with the solid obtained on evaporating to dryness in vacuo the another liquor from the reaction described in (A) (0.9 g), were dissolved in water (150 ml). To the solution was added saturated aqueous barium hydroxide solution (75 ml), and the mixture was stirred at room temperature for 6 hours. A stream of carbon dioxide was then passed through the mixture for a few minutes, and the resulting white precipitate of barium carbonate and other solid matter was removed by filtration, the filtrate being evaporated in vacuo to dryness. The residual solid was extracted with methanol, and the methanolic solution was evaporated in vacuo to dryness. A solution of the residual solid in water (15 ml) with its pH adjusted to 5.5 by addition of sufficient 1N hydrochloric acid, was passed down a resin column (Amberlite CG120, $NH_4^+$ form). Elution was performed using N/15 ammonium hydroxide solution, and a collected fraction was evaporated in vacuo to dryness, the residual solid then being azeotroped in turn with ethanol and toluene. The vacuum-dried solid (1.4 g) was shown by thin layer chromatographic and electrophoretic evidence to consist substantially of a single product, identified as 1,3,3''-tri(N-carbomethoxy)kanamycin A monohydrate, with the following characterising features:

Thin layer chromatography, silica:
Product of (B) $R_f$ = 0.73 (Solvent system was an equipart
Cf. Product of (A) $R_f$ = 0.70 mixture of methanol and 0.880 ammonia)
Thin layer electrophoresis:
Product of (B) $R_f$ = 0.37
Cf. Product of (A) $R_f$ = 0.12 (main) 0.37 (trace)
(The electrolyte was an equipart mixture of acetic and formic acids, giving a pH value of 2, and a potential difference of 900 volts for 55 minutes was applied across the ends of the silica plate. Detection was carried out as described under this heading in Example 3).

Analysis: Found: C, 42.19; H, 6.21; N, 7.93%, Required for $C_{24}H_{42}N_4O_{17}.H_2O$: C, 42.60; H, 6.55; N, 8.28%.

CHARACTERIZATION OF PRODUCT

To a suspension of the product of (B) (0.5 g) in dry methanol (10 ml) was added acetic anhydride (0.5 g), and the mixture was stirred for 16 hours at room temperature. Excess methanol was added, and the mixture was evaporated in vacuo to dryness affording a solid (0.5 g). Thin layer chromatographic and electrophoretic evidence indicated that the residual solid, m.p. 200° C (with decomposition), consisted substantially of a single product, identified as 6'-N-acetyl-1,3,3''-tri(-Ncarbomethoxy)kanamycin A dihydrate, with the following characterising features:

Thin layer chromatography, silica:
Acetylated product $R_f$ = 0.77 (Solvent system was an c.f. Product of (B) $R_f$ = 0.73 equipart mixture of methanol and 0.880 ammonia)
Thin layer electrophoresis:
Acetylated product $R_f$ = 0.07
c.f. Product of (A) $R_f$ = 0.10 (main) 0.37 (trace)
(The conditions for this were as described under this heading in Example 3).
Analysis: Found: C, 42,92; H, 6.27; N, 7.49%, Required for $C_{26}H_{44}N_4O_{18}.2H_2O$: C, 42.40; H, 6.57; N, 7.61%,
Nuclear magnetic resonance spectrum, deuterated pyridine:
Major peaks at
τ6.40 (singlet, 3H of $-CO_2CH_3$)
τ6.42 (single, 3H of $-CO_2CH_3$)
τ6.49 (singlet, 3H of $CO_2CH_3$)
τ8.0 (singlet, 3H of $OCOCH_3$)

It was concluded that only one of the four amino groups in the molecule had been acylated by this procedure, and that the attempted mono-deprotection process described in the Example had indeed resulted in the loss of only one of the carbomethoxy protecting groups from the four protected amino groups originally present in the molecule.

EXAMPLE 8

1,3,3''-Tri(N-t-butoxycarbonyl)kanamycin A

6'-N-benzyloxycarbonylkanamycin A (1.5 g; 0.0032 mole) was dissolved in 50% aqueous dioxan (200 ml) and triethylamine (3.7 g; 0.037 mole) was added. A solution of t-butyl azidoformate (5.5 g; 0.038 mole) in dioxan (20 ml) was added dropwise and the stirred reaction was then heated to 80° for 8 hours. After cooling, a further quantity of triethylamine was added (0.7 g; 0.007 mole), followed by t-butyl azidoformate (1 g; 0.007mole) in 5 ml dioxan, and the reaction was reheated to 80° C. for a further period of 8 hours. After cooling, the reaction was diluted with 600 ml of water, and the precipitate filtered off, washed with water and ether, and dried. A yield of 0.7 g of crude 6'-N-benzyloxycarbonyl-1,3,3''-tri(N-t-butyloxycarbonyl)kanamycin A was obtained. The crude material was dissolved in liquid ammonia (100 ml), which had been distilled into the reaction vessel, and the solution allowed to reflux. Small pieces of sodium metal were added, allowing the blue coloration of the solution to disappear before the next addition was made. When the blue color persisted for longer than 5 minutes, an excess of ammonium chloride was added, and the ammonia allowed to evaporate. The residue was dissolved in 100 ml water and the solution immediately neutralised with 2N hydrochloric acid. The water was removed by evaporation under reduced pressure and the organic portion of the residue was dissolved in 75 ml dimethylformamide. After filtration the solution was poured into diethyl ether (300 ml) and the resultant precipitate was filtered off and washed with ether. The crude product was redissolved in 40 ml water and the pH adjusted to 5.5, using 2N hydrochloric acid. The solution was then chromatographed on a column containing CG 50 ion exchange resin (100 ml; $NH_4^+$ form) and eluted with water. The product was contained in fractions 17-31 which were evaporated to dryness, the residual solid being identified as 1,3,3''-tri(N-t-butoxycarbonyl)kanamycin A by methods similar to those used to identify the product of Example 7.

EXAMPLE 9

1,3,2',3''-Tetra(N-t-butoxycarbonyl)kanamycin B

A. To a solution of 6'-N-benzyloxycarbonylkanamycin B (24.0 g; 0.0387 mole) in a mixture of dioxan (134 ml.) and water (66 ml) was added t-butyl azidoformate (59.0 g; 0.465 mole) and triethylamine (47.2 g; 0.465 mole). The resultant mixture was heated to 80° C. with vigorous stirring for 18 hours. After cooling the resultant pasty mixture was poured into two liters of an ice/water mixture, a pale brown precipitate being formed. The precipitate was filtered off in vacuo, washed well with water, then with ether, and finally dried in vacuo to give 6'-N-benzyloxycarbonyl-tetra(N-t-butoxycarbonyl)kanamycin B (32.4 g; 82.2% yield).

The infra red spectrum of the product showed a broad band at 1680 cm-1, associated with urethane groups. Thin layer chromatography on Merck precoated plates (Silica Gel 60 F254), eluted with an 80 : 20 : 5 mixture of chloroform : methanol : 0.880 ammonium hydroxide, yielded a single component of $R_f$ 0.73, visualised with (a) 5% hydrochloric acid/methanol (b) t-butyl hypochlorite/cyclohexane and finally (c) starch/potassium iodide solution.

B. A solution of 6'-N-benzyloxycarbonyl-tetra(N-t-butoxycarbonyl)-kanamycin B (31.9 g; 0.0312 mole) in 1.0 liter of a 2/1 methanol/water mixture was adjusted to pH4 with glacial acetic acid. To the solution was added 30% palladium/carbon catalyst (5.0 g) and the mixture hydrogenated at 30° under a pressure of 50 psi. Upon completion of uptake (12 hours) the solution was cooled and filtered to remove the catalyst. The filtrate was adjusted to pH7 with ammonium hydroxide solution and evaporated to about 70 ml when the product crystallised from solution. This material was filtered under vacuum and dried at 45°, to give 1,3,2',3''-tetra(N-t-butoxycarbonyl)kanamycin B (14.24 g; 51.7% yield) m.p. 180° C. with decomposition.

Analysis: calculated for $C_{38}H_{69}N_5O_{18}.H_2O$: C 50.71, H 7.73, N 7.78 Found C 50.14, H 7.86, N 7.79.
The infra-red spectrum showed a broad urethane band at 1680 cm$^{-1}$. A quantitative NMR spectrogram confirmed the presence of four t-butyl groups. Thin layer chromatography as in (A) yielded a single component of $R_f$ 0.29.

EXAMPLE 9A 1,3,2',3''-Tetra(N-t-butoxycarbonyl)tobramycin

The title compound is prepared from 6'-N-benzyloxycarbonyltobramycin by reaction with t-butyl azidoformate, and subsequent solvolysis with acetic acid at pH 4, using the procedure of Example 9.

EXAMPLE 10

1,3,2',3''-Tetra(N-t-butoxycarbonyl)kanamycin B

A. To a stirred solution of kanamycin B (5.0 g; 0.00963 mole) and triethylamine (2.68 g; 0.01926 mole) in 175 ml of a 2/1 dioxan/water mixture at 0°–2° C. was added N-(benzyloxycarbonyloxy)succinimide (2.64 g; 0.0106 mole) in 25 ml of the same solvent over a period of one hour. The solution was placed in a refrigerator overnight and then evaporated to dryness in vacuo. The residue was dissolved in 200 ml water and extracted 5 times with 50 ml. of n-butanol. The combined n-butanol layers were back-washed with 50 ml water and the aqueous layer evaporated to dryness to give 5.9 g of crude 6'-N-benzyloxycarbonylkamamycin B.

B. The crude product from (A) was dissolved in 100 ml of a 2/1 dioxan/water mixture containing triethylamine (16.1 ml; 0.116 mole) and t-butyl azidoformate (16.5 g; 0.116 mole) was added. The vigorously stirred mixture was heated to 80° C. and held for 18 hours. After cooling, the resulting gelatinous mixture was poured into 1 liter of an ice/water mixture and the buff-colored product which separated was filtered off under vacuum, washed well with water and dried in vacuo at 40° C. to yield 4.9 g of crude 6'-N-benzyloxycarbonyltetra(N-t-butoxycarbonyl)kanamycin B.

C. The crude product from (B) was dissolved in 70 ml distilled liquid ammonia at reflux under anhydrous conditions. Small pieces of clean sodium metal were added to the stirred solution until a persistent blue coloration had been maintained for 5 minutes. Excess sodium was decomposed by the addition of a small amount of anhydrous ammonium chloride. After evaporation of the ammonia the residue was suspended, with stirring, in 30 ml of water and quickly neutralised to pH7 with 1N aqueous hydrochloric acid. The product was filtered off and dried in vacuo at 40° to yield 1,3,2',3''-tetra(N-t-butoxycarbonyl)-kanamycin B (2.9 g; 34.1% overall yield from kanamycin B), m.p. 180 with decomposition. The product was identified by its infrared spectrum, and by thin-layer chromatography, as being the same as the product of Example 9.

EXAMPLE 11

6'-N-Benzylneamine

A. To a stirred solution of 5,6-O-cyclohexylidene-2',1,3-tri(N-carbomethoxy)neamine (6.3 g, 0.011 moles) in methanol (50 ml), prepared by the method described in Example 1, was added benzaldehyde (1.9 ml. 0.017 moles), and stirring at room temperature was continued for 24 hours. Sodium borohydride (0.63 g, 0.017 moles) was then added, and stirring was continued for a further 2 hours. Neutralisation of the reaction mixture was effected by adding thereto a sufficient quantity of dilute hydrochloric acid, after which the mixture was evaporated in vacuo to dryness, affording a white solid. The solid was extracted with chloroform and the chloroform solution was washed twice with water and evaporated in vacuo to dryness. The resulting solid residue was dissolved in dry toluene and evaporated in vacuo to dryness, affording 5.0 g of 6'-N-benzyl-5,6-O-cyclohexylidene-2',1,3-tri(-N-carbomethoxy)neamine as a white solid, m.p. 140°–145° C with decomposition.

Analysis: Found: C, 56.55; H, 7.05; N, 7.83%, Required for $C_{31}H_{46}N_4O_{12}$: C, 55.84; H, 6.96; N, 8.40%.

B. A heterogeneous mixture of the product of (A) (0.5 g, 0.00075 moles) and 4N aqueous barium hydroxide solution (25 ml, 0.013 moles $Ba(OH)_2$) was stirred at 90° C. overnight, after which a stream of carbon dioxide was passed through the mixture until the solution was neutral ($pH_7$). The resulting precipitate of barium carbonate and other solid matter was then removed by filtration, and dilute hydrochloric acid was added to the filtrate until it was at pH 1, whereafter the solution was heated over a steam bath for 2 hours. Neutralisation of the solution by addition of a sufficient quantity of aqueous sodium bicarbonate solution, followed by evaporation in vacuo to dryness, afforded a white solid which was extracted three times with boiling methanol. The methanolic solutions were combined and evaporated in vacuo to dryness, the resulting solid residue then being dissolved in a small quantity of water the aqueous solution being acidified to pH 5 by addition of a sufficient quantity of dilute sulfuric acid. The aqueous acidic solution was passed down an ion-exchange column of Amberlite IRC-50 resin (ammonium ion form), (Amberlite is a registered Trade Mark), eluting in turn with distilled water, to remove inorganic solids, and 1N ammonium hydroxide solution. A fraction collected was evaporated in vacuo to dryness and the residue (0.18 g) was crystallised from isopropanol to yield 77 mg (first crop) of 6'-N-benzylneamine hydrate, m.p. 177°–179° C with decomposition.

Analysis: Found: C,53.78; H, 8.29; N, 13.20%, Required for $C_{19}H_{32}N_4O_6.H_2O$: C, 53.01; H, 7.96; N, 13.02%.

EXAMPLES 12 to 31

The following derivatives and analogues of the product of Example 11 were prepared by a similar procedure, starting from 5,6-O-cyclohexylidene-2',-1,3-tri(N-carbomethoxy)neamine and the appropriately substituted benzaldehyde or heterocyclic aldehyde R-CHO. Tables I and II show the structures of the compounds prepared together with melting points and/or elemental analysis in some cases. In these and other cases, the identities of the compounds were confirmed by thin layer chromatographic or electrophoretic analysis with standard reference compounds and by nuclear magnetic resonance and mass spectrographic methods.

TABLE I

[Structure: neamine derivative with R⁷ substituted benzyl group, shown as NHCH₂-(phenyl with R⁷), with sugar ring (HO, OH, NH₂) linked via O to aminocyclohexane (H₂N, OH, OH, NH₂·H₂O)]

| Example | R⁷ | m.p. ° C | Analysis% (Theoretical in brackets) C | H | N |
|---|---|---|---|---|---|
| 12 | 4-Cl | 180–183° (dec.) | | | |
| 13 | 4-CH₃ | 200–203° (dec.) | 53.96 (54.04 | 7.73 8.16 | 12.79 12.61) |
| 14 | 4-CH₃O | 200–203° | 53.05 (52.16 | 6.87 7.88 | 11.44 12.77) |
| 15 | 2-OH | 176–178° (dec.) | 51.20 (51.11 | 7.40 7.68 | 11.96 12.55) |
| 16 | 4-N(CH₃)₂ | 186–188° (dec.) | 54.79 (55.36 | 8.16 8.19 | 15.44 15.38)* |
| 17 | 4-CF₃ | 192–194° (dec.) | 47.79 (48.19 | 6.12 6.67 | 11.41 11.24) |
| 18 | 3,4-diCl | 181–184° (dec.) | 45.99 (45.69 | 6.26 6.46 | 11.39 11.22) |
| 19 | 3-Cl | 170–173° (dec.) | 48.33 (49.08 | 6.68 7.15 | 11.99 12.05) |
| 20 | 4-NH₂** | 170–173° (dec.) | 50.69 (51.22 | 7.09 7.92 | 15.52 15.73) |
| 21 | 4-COOH | 226–230° (dec.) | 47.87 (50.62 | 6.99 7.22 | 11.16 11.81) |
| 22 | 3-CF₃ | 180–185° | — | | |
| 23 | 3-CH₃ | — | — | | |
| 24 | 2-CH₃ | — | — | | |

*calculated for the anhydrous compound
** prepared by using 4-acetamido-benzaldehyde starting material

TABLE II

[Structure: neamine derivative with NHCH₂—R substituent, sugar ring (HO, HO, NH₂) linked via O to aminocyclohexane (NH₂, HO, OH, NH₂·H₂O)]

| Example | R | m.p.° C | Analysis % (theoretical in brackets) C | H | N |
|---|---|---|---|---|---|
| 25 | 2-thienyl | 198–200° (dec.) | 47.77 (46.74 | 6.85 7.38 | 12.20 12.88) |
| 26 | 2-indolyl | 127–129° (dec.) | — | | |
| 27 | 2-pyrryl | 81–84° (dec.) | — | | |
| 28 | 2-pyridyl | 125–130° (dec.) | 50.19 (50.21 | 7.25 7.65 | 15.62 16.24) |
| 29 | 5-methyl-2-thienyl | 197–201° (dec.) | — | | |
| 30 | 4-pyridyl | 158° (dec.) | 49.03 (50.10 | 7.54 7.65 | 15.57 16.24) |
| 31 | 6-chloro-3-pyridyl | 100–103° (dec.) | — | | |

EXAMPLE 32

6′-N-Benzylneamine

A. To a solution of 5,6-O-cyclohexylidene-2′, 1,3-tri(N-carbomethoxy)neamine (1.0 g) in absolute ethanol (40 ml) was added benzaldehyde (0.5 g), and the resulting solution was submitted to hydrogenation at room temperature and 40 p.s.i pressure in the presence of platinum oxide (20 mg). After 2 hours, the reaction mixture was filtered to remove catalyst and other solid matter, and the filtrate was evaporated in vacuo to dryness, affording a solid. The latter was washed with n-hexane to remove excess benzaldehyde, and then dried in vacuo over several hours. Produced was 6′-N-benzyl-5,6-O-cyclohexylidene-2′, 1,3-tri(N-carbomethoxy)neamine.

B. The product of (A) was hydrolysed in aqueous barium hydroxide solution and then in aqueous hydrochloric acid solution, by a procedure similar to that described in part (B) of Example 11, affording 6′-N-benzylneamine hydrate, identified as such by comparison of its thin layer electrophoresis and nuclear magnetic resonance spectrum with those of the product of Example 11.

EXAMPLE 33

6'-N-Benzylneamine

The title compound has also been prepared as its hydrate by the method of Example 11(A) followed by hydrolysis in aqueous hydrochloric acid solution, using as starting material 2',1,3-tri(N-tertiarybutyloxycarbonyl)-neamine. The latter compound was prepared from neamine by the method of Example 5(A) and (C) omitting stage (B) in which the cyclohexylidene group is introduced.

EXAMPLES 34 to 64

Using the method of Example 33, i.e., the procedure of Example 11(A) followed by hydrolysis in aqueous hydrochloric acid solution to remove the tertiary-butyloxycarbonyl groups, the following derivatives of kanamycin B were prepared from 1,3,2',3''-tetra(N-t-butoxycarbonyl)kanamycin B (prepared as described in Example 9 or Example 10) and the appropriate aldehyde R-CHO. Tables III and IV show the structures of the compounds prepared together with the results of thin layer chromatographic (T.L.C.) and electrophoretic (T.L.E.) analysis, used to identify the compounds by comparison with kanamycin B as reference standard. In each case the appropriate $R_f$ value is shown for the compound, compared with that for kanamycin B (K-B). These compounds have indeterminate melting points and the elemental analyses of such high molecular weight compounds are not meaningful.

TABLE III

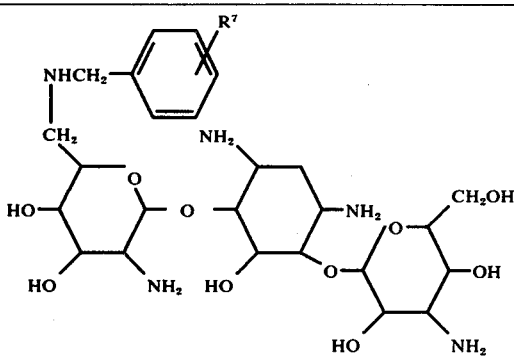

| Example | $R^7$ | $R_f$ (T.L.C.)[1] | $R_f$ (T.L.E.)[2] |
|---|---|---|---|
| 34 | H | — | 0.3 (K-B 0.5) |
| 35 | 4-OCH₃ | — | 0.15 (K-B 0.5) |
| 36 | 4-Cl | — | 0.09 (K-B 0.34) |
| 37 | 4-CF₃ | 0.58 (K-B 0.38) | 0.21 ( '' ) |
| 38 | 3-OCH₃ | 0.6 (K-B 0.3) | 0.3 (K-B 0.6) |
| 39 | 2-OCH₃ | 0.5 (K-B 0.2) | 0.2 (K-B 0.5) |
| 40 | 2-CH₃ | 0.55 (K-B 0.25) | 0.2 (K-B 0.5) |
| 41 | 3-CH₃ | 0.6 (K-B 0.2) | 0.3 (K-B 0.6) |
| 42 | 3,5-di-OCH₃ | — | 0.29 (K-B 0.41) |
| 43 | 3,4,5-tri-OCH₃ | — | 0.32 (K-B 0.43) |
| 44 | 2-OH | 0.5 (K-B 0.2) | 0.3 (K-B 0.5) |
| 45 | 3,4-di-OCH₃ | 0.60 (K-B 0.38) | 0.23 (K-B 0.40) |
| 46 | 4-C₆H₅ | 0.60 (K-B 0.3) | 0.50 (K-B 0.5) |
| 47 | 4-COOH | 0.7 (K-B 0.3) | 0.3 (K-B 0.6) |
| 48 | 2-CH₂OH | 0.65 (K-B 0.2) | 0.3 (K-B 0.5) |
| 49 | 2-COOH | 0.7 (K-B 0.2) | .15 (K-B 0.5) |

TABLE III-continued

| Example | $R^7$ | $R_f$ (T.L.C.)[1] | $R_f$ (T.L.E.)[2] |
|---|---|---|---|
| 50 | 3,4-di-Cl | — | 0.1 (K-B 0.4) |
| 51 | 4-CH₃ | 0.58 (K-B 0.31) | 0.18 (K-B 0.40) |
| 52 | 4-OH | 0.58 (K-B 0.31) | 0.29 (K-B 0.39) |
| 53 | 4-N(CH₃)₂ | 0.65 (K-B 0.40) | 0.22 (K-B 0.36) |
| 54 | 4-F | 0.8 (K-B 0.3) | 0.2 (K-B 0.5) |
| 55 | 2-OCH₂C₆H₅ | 0.6 (K-B 0.3) | 0.1 (K-B 0.4) |
| 56 | 4-Br | 0.65 (K-B 0.35) | 0.20 (K-B 0.53) |
| 57 | 4-NH₂* | — | 0.30 (K-B 0.40) |

*prepared by using 4-acetamido-benzaldehyde starting material.
[1] medium: 2/1 methanol/ 0.880 amonia mixture
[2] 900 volts for 50 minutes in formic/acetic buffer (pH 2).

TABLE IV

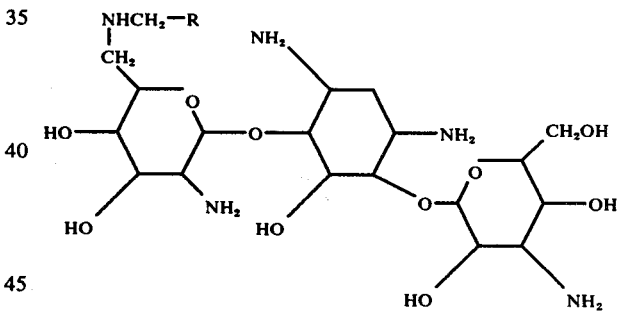

| Example | R | Rf (T.L.C.)[1] | Rf (T.L.E.)[2] |
|---|---|---|---|
| 58 | 2-furyl | — | 0.25 (K-B 0.42) |
| 59 | 2-naphthyl | 0.5 (K-B 0.3) | 0.5 (K-B 0.5) |
| 60 | 2-thienyl | — | 0.26 (K-B 0.45) |
| 61 | 5-methyl-2-thienyl | — | 0.6 (K-B 0.35) |
| 62 | 9-phenanthryl | 0.6 (K-B 0.3) | 0.05 (K-B 0.5) |
| 63 | 1-naphthyl | — | 0.18 (K-B 0.47) |
| 64 | 2-pyridyl | — | 0.25 (K-B 0.5) |

[1] medium: 2/1 methanol/ 0.880 ammonia mixture
[2] 900 volts for 50 minutes in formic/acetic buffer (pH 2).

EXAMPLE 65

6'-N-Benzylkanamycin B

Kanamycin B free base (3 g; 0.0062 mole) was dissolved in a mixture of dioxan (25 ml) and water (15 ml). Triethylamine (1.17 g; 0.0116 mole) was added and the solution cooled to 5° C. in ice. Benzyl chloride (1.46 g; 0.0115 mole) was added in dioxan (10 ml) over a 1 hour period. A solid was obtained by concentrating at 40° C./15mm, extracting the residue three times with ether and evaporating the combined extracts. This solid was dissolved in water (50 ml) and acidified with 0.1N HCl to pH 5.5 Ion exchange chromatography was carried out on a column of "Amberlite" CG 50 resin (ammonium form), eluting with water initially and then with N/15 aqueous ammonia. On bulking and concentrating the appropriate fractions, as monitored by thin layer electrophoresis, 0.5 g of 6'-N-benzylkanamycin B was obtained, identical with the product of Example 34.

EXAMPLE 66

6'-N-Benzylkanamycin B

A. Kanamycin B free base (10 g; 0.021 mole) was dissolved in a mixture of water (40 ml) and dioxan (30 ml). After cooling to 0° C. in an ice-salt bath, succinimido benzoate (5.0 g; 0.023 mole) in dioxan (30 ml) was added over 5 hours at a very slow drop rate to maintain the temperature in the range from 0° to 5° C. After standing at 0° C. overnight the solvent was removed from the reaction mixture under vacuum by codistillation three times with dry toluene. The resulting gum was chromatographed on Amberlite CG 50 resin (ammonium form) using a gradient of 0.05 to 0.15N aqueous ammonia as elutant. On bulking and concentrating the relevant fractions 6.3 g of 6'-N-benzoyl-kanamycin B was obtained (49% yield).

B. A molar solution of diborane in tetrahydrofuran (137 ml) was added to dry tetrahydrofuran (70 ml) and heated to a gentle reflux under a nitrogen atmosphere. A solution of 6'-N-benzoylkanamycin B (6.2 6) in tetrahydrofuran (60 ml) was added over a 7 hour period. After stirring the reaction overnight at room temperature, the excess diborane was decomposed with water and the whole basified to pH 9.5 with 0.1N aqueous sodium hydroxide solution. The solution was concentrated to about 35 ml by codistillation three times with water under vacuum, and acidified with 0.1N HCl to pH 5.5. Ion exchange chromatography on a column of Amberlite CG 50 resin (ammonium form) using a gradient of 0.05N to 0.15N aqueous ammonia as elutant yielded 1.9 g of 6'-N-benzyl-kanamycin B (17% overall yield from kanamycin B) from the relevant fractions.

EXAMPLE 67

6'-N-(2-Naphthylmethyl)kanamycin A

A. A solution of kanamycin A sulfate (7 g) in water (40 ml) was treated with triethylamine (4 ml) and slowly added to pyridine (40 ml). The solution was cooled to below 10°, treated with one molar equivalent of 2-naphthoyl chloride and stirred at room temperature overnight. After evaporation to dryness under reduced pressure, water was added twice and evaporated. The solid residue was then dissolved in water (100 ml) filtered, and the filtrate was adjusted to pH 5.5, put on an ion-exchange column of Amberlite CG 50 resin (ammonium form), washed first with water and then eluted with N/15 aqueous ammonia. The relevant fractions were combined and evaporated to yield 0.6 g of 6'-N-(2-naphthoyl)kanamycin A as a white solid, m.p. above 260°. Infra-red spectrography showed an a amide band at 1640 cm$^{-1}$. The product was identified by thin layer chromatography (Rf 0.6, kanamycin A Rf 0.2) and electrophoresis (Rf 0.40, relative to kanamycin A), using methods as in Examples 34–64.

B. The product of (A) (0.2 g) was dissolved in trifluroracetic acid (2 ml) and evaporated to dryness to yield the trifluoroacetic acid addition salt. This was dissolved in dry tetrahydrofuran and treated with a molar solution of diborane in tetrahydrofuran (4 ml). After standing at room temperature for 4 days, water was added (20 ml) and methanol was then added and evaporated three times to remove boric acid as methyl borate. The pH was adjusted to 1.0 with 5N-HCl and then to 5.0 with saturated aqueous sodium bicarbonate solution. The solution was then put on an ion-exchange column of Amberlite CG 50 resin (ammonium form), washed with water and then eluted with N/20 aqueous ammonia. The relevant fractions were combined and evaporated. Methanol was then added and evaporated to yield 0.086 g of 6'-N(2-naphthylmethyl)kanamycin A as a white solid, m.p. about 205° (decomposed), identified by thin layer chromatography (2/1 methanol-/ammonia, Rf 0.60) and electrophoresis (Rf 0.35 relative to kanamycin A, and by mass spectrometry (field desorption) showing a strong P + 1 peak at 625.

EXAMPLE 68

6'-N-(4-Biphenylylmethyl)kanamycin A

The title compound was prepared, and identified by thin-layer chromatography ($R_f$ 0.5) and electrophoresis ($R_f$ 0.1 relative to kanamycin A), using the method of Example 67, and replacing the 2-naphthoyl chloride by 4-phenylbenzoyl chloride.

EXAMPLE 69

6-N-(4-Acetamidobenzyl)kanamycin A

A solution of kanamycin A sulfate (2.28 g; 0.0041 mole) in water (150 ml) was treated with sodium carbonate (1.92 g) and cooled on an ice bath. A solution of 4-acetamidobenzaldehyde (0.74 g; 0.0046 mole) in methanol (25 ml) was then added slowly over about 10 minutes and the reaction mixture was left to stand at 0° for 3 days. Sodium borohydride (0.50 g; 0.013 mole) was then added and the mixture stirred overnight at room temperature. After concentration to 50 ml by evaporation under vacuum, the pH of the solution was adjusted to 5.0 with 5N HCl and put onto an ion-exchange column of Amberlite CG 50 resin (ammonium form), washed first with water and then eluted with N/15 aqueous ammonia. Evaporation of the relevant fractions yielded 0.193 g of 6'-N-(4-acetamidobenzyl)-kanamycin A, identified by thin-layer electrophoresis (Rf 0.45, relative to kanamycin A).

EXAMPLES 70 to 77

Using the method of Example 69, the compounds shown in Table V were prepared from kanamycin A sulfate and the appropriate aldehyde R-CHO.

TABLE V

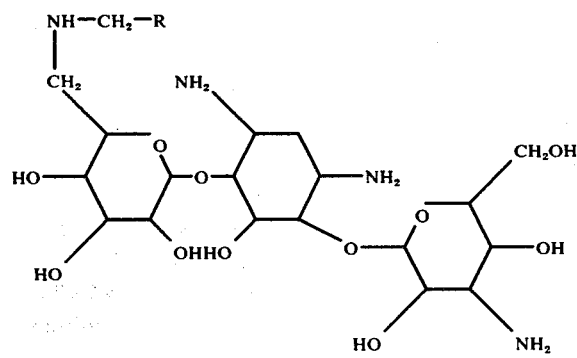

| Example | R | Rf (T.L.C.)[1] | (Rf (T.L.E.)[3] |
|---|---|---|---|
| 70 | p-hydroxyphenyl | 0.6 (K-A 0.2) | 0.6 |
| 71 | p-(N,N-dimethyl amino)phenyl | 0.6 (K-A 0.2) | 0.3 |
| 72 | phenyl | — | 0.7 |
| 73 | 4-pyridyl | 0.3 (K-A 0.2) | — |
| 74 | p-carboxyphenyl | — | 0.55 |
| 75 | p-nitrophenyl | — | 0.5 |
| 76 | o-hydroxyphenyl | — | 0.6 |
| 77* | p-aminophenyl | — | 0.6 |

*prepared by hydrogenation of the compound of Example 75 with Raney nickel.
[1] medium: 2/1 methanol/ 0.880 ammonia mixture
[3] relative to kanamycin A, conditions as before.

EXAMPLE 78 TO 105

The procedure of Example 11 is repeated, except that the benzaldehyde used therein is replaced by an equimolar of the appropriate aldehyde (R-CHO), to produce the following compounds.

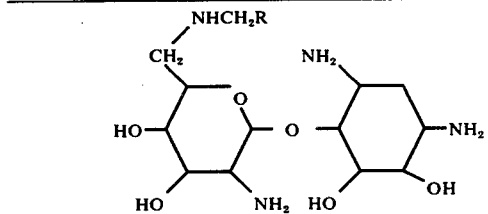

| Example | R |
|---|---|
| 78 | 3-fluorophenyl |
| 79 | 4-iodophenyl |
| 80 | 3-(N,N-diethylamino)phenyl |
| 81 | 3-(N,N-dibutylamino)phenyl |
| 82 | 4-(N,N-dihexylamino)phenyl |
| 83 | 4-(N-methylamino)phenyl |
| 84 | 2-ethoxyphenyl |
| 85 | 4-butoxyphenyl |
| 86 | 3-isoamyloxyphenyl |
| 87 | 4-(benzyloxy)phenyl |
| 88 | 3-biphenylyl |
| 89 | 4-isopropylphenyl |
| 90 | 4-n-hexylphenyl |
| 91 | 3,4-dimethoxyphenyl |
| 92 | 3,4-dimethoxyphenyl |
| 93 | 3-chloro-4-methoxyphenyl |
| 94 | 1-naphthyl |
| 95 | 2-naphthyl |
| 96 | 1-anthryl |
| 97 | 2-phenanthryl |
| 98 | 2-furyl |
| 99 | 3-furyl |
| 100 | 3-thienyl |
| 101 | 4-pyrimidyl |
| 102 | 4-imidazolyl |
| 103 | 2-quinolyl |
| 104 | 4-quinolyl |
| 105 | 3-indolyl |

EXAMPLES 106 TO 172

Reaction of kanamycin A sulfate, kanamycin B sulfate, or tobramycin sulfate, as appropriate, with the requisite aldehyde (R-CHO9, according to the procedure of Example 69, affords the following congeners.

| Example | R | $R^6$ | $R^2$ |
|---|---|---|---|
| 106 | 2-fluorophenyl | OH | OH |
| 107 | 3-chlorophenyl | OH | OH |
| 108 | 4-iodophenyl | OH | OH |
| 109 | 4-(N-methylamino)phenyl | OH | OH |
| 110 | 4-(N,N-diethylamino)phenyl | OH | OH |
| 111 | 3-methoxyphenyl | OH | OH |
| 112 | 4-isopropoxyphenyl | OH | OH |
| 113 | 3-methylphenyl | OH | OH |
| 114 | 4-isopropylphenyl | OH | OH |
| 115 | 4-(trifluoromethyl)phenyl | OH | OH |
| 116 | 4-(isopropoxycarbonyl)phenyl | OH | OH |
| 117 | 4-(n-hexyloxycarbonyl)phenyl | OH | OH |
| 118 | 4-biphenylyl | OH | OH |
| 119 | 1-naphthyl | OH | OH |
| 120 | 2-anthryl | OH | OH |
| 121 | 2-furyl | OH | OH |
| 122 | 2-pyrimidyl | OH | OH |
| 123 | 2-quinolyl | OH | OH |
| 124 | 3-chloro-4-hydroxyphenyl | OH | OH |
| 125 | 2,4-dimethoxyphenyl | OH | OH |
| 126 | 2-(N-ethylamino)phenyl | OH | $NH_2$ |
| 127 | 2-(N-hexylamino)phenyl | OH | $NH_2$ |
| 128 | 4-(N,N-diisopropylamino)phenyl | OH | $NH_2$ |
| 129 | 4-(N,N-dihexylamino)phenyl | OH | $NH_2$ |
| 130 | 4-propionamidophenyl | OH | $NH_2$ |
| 131 | 4-butyramidophenyl | OH | $NH_2$ |
| 132 | 4-hexanamidophenyl | OH | $NH_2$ |
| 133 | 3-ethoxyphenyl | OH | $NH_2$ |
| 134 | 4-tolyl | OH | $NH_2$ |
| 135 | 4-n-hexyloxyphenyl | OH | $NH_2$ |
| 136 | 2-methoxycarbonylphenyl | OH | $NH_2$ |
| 137 | 4-n-hexylphenyl | OH | $NH_2$ |
| 138 | 4-ethoxycarbonylphenyl | OH | $NH_2$ |
| 139 | 3-chloro-4-methoxyphenyl | OH | $NH_2$ |
| 140 | 3-thienyl | OH | $NH_2$ |
| 141 | 4-pyrimidyl | OH | $NH_2$ |
| 142 | 4-imidazolyl | OH | $NH_2$ |
| 143 | 2-indolyl | OH | $NH_2$ |
| 144 | 2-fluorophenyl | H | $NH_2$ |
| 145 | 4-chlorophenyl | H | $NH_2$ |
| 146 | 3-hydroxyphenyl | H | $NH_2$ |
| 147 | 2-aminophenol | H | $NH_{12}$ |
| 148 | 2-(N-methylamino)phenyl | H | $NH_2$ |
| 149 | 4-(N,N-diethylamino)phenyl | H | $NH_2$ |
| 150 | 4-(N,N-di-n-pentylamino)phenyl | H | $NH_2$ |
| 151 | 2-acetamidophenyl | H | $NH_2$ |
| 152 | 4-isobutyramidophenyl | H | $NH_2$ |
| 153 | 4-nitrophenyl | H | $NH_2$ |
| 154 | 2-methoxyphenyl | H | $NH_2$ |
| 155 | 3-isopropoxyphenyl | H | $NH_2$ |
| 156 | 3-tolyl | H | $NH_2$ |
| 157 | 4-isobutylphenyl | H | $NH_2$ |
| 158 | 4-benzyloxyphenyl | H | $NH_2$ |
| 159 | 2-trifluoromethylphenyl | H | $NH_2$ |
| 160 | 4-carboxyphenyl | H | $NH_2$ |
| 161 | 2-methoxycarbonylphenyl | H | $NH_2$ |
| 162 | 4-valeroyloxycarbonyl | H | $NH_2$ |
| 163 | 4-biphenylyl | H | $NH_2$ |
| 164 | 2-naphthyl | H | $NH_2$ |
| 165 | 2-anthryl | H | $NH_2$ |
| 166 | 2-pyridyl | H | $NH_2$ |
| 167 | 3-furyl | H | $NH_2$ |
| 168 | 2-thienyl | H | $NH_2$ |
| 169 | 4-pyrimidyl | H | $NH_2$ |
| 170 | 2-quinolyl | H | $NH_2$ |

-continued

| | | | |
|---|---|---|---|
| 171 | 2-indolyl | H | NH₂ |
| 172 | 3-chloro-4-hydroxyphenyl | H | NH₂ |

EXAMPLE 173 TO 180

Reaction of neamine with the appropriate aldehyde, according to the procedure of Example 69, produces:

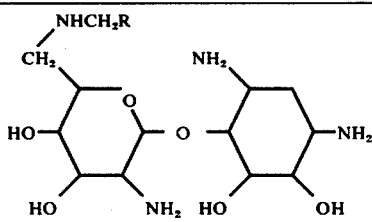

| Example | R |
|---|---|
| 173 | 2-acetamidophenyl |
| 174 | 4-isobutyramidophenyl |
| 175 | 4-n-hexanamidophenyl |
| 176 | 4-nitrophenyl |
| 177 | 2-methoxycarbonylphenyl |
| 178 | 3-ethoxycarbonylphenyl |
| 179 | 3-isobutoxyphenyl |
| 180 | 4-n-hexyloxyphenyl |

EXAMPLE 181

In Vitro Antibacterial Activities of 6'-N-substituted Neamines

| Compound (identified by Example number) | M.I.C. (μg/ml) | | |
|---|---|---|---|
| | Proteus mirabilis | Pseudomonas aeruginosa | Staphylococcus aureus |
| 11 | 50 | >100 | 50 |
| 12 | >100 | 6.25 | 50 |
| 13 | 50 | 12.5 | 50 |
| 14 | 100 | 50 | 50 |
| 15 | 50 | 100 | 50 |
| 16 | >100 | 50 | 25 |
| 17 | >100 | 1.56 | 100 |
| 19 | >100 | 25 | >100 |
| 20 | 50 | >100 | 12.5 |
| 25 | >100 | >100 | 50 |
| 29 | >100 | 50 | >100 |

EXAMPLE 182

In Vitro Antibacterial Activities of 6'-N-substituted Kanamycins

| Compound (identified by Example number) | M.I.C. (μg/ml) | | | | | |
|---|---|---|---|---|---|---|
| | E. Coli | Klebsiella pneumoniae | Proteus mirabilis | Pseudomonas aeruginosa | Staphylococcus aureus | siella faecalis |
| 34 | 1.56 | 1.56 | 12.5 | >100 | 0.19 | 25 |
| 35 | 3.12 | 3.12 | 25 | >100 | 0.39 | 25 |
| 36 | 3.12 | 3.12 | 25 | 50 | 1.56 | 25 |
| 37 | 12.5 | 12.5 | 100 | >100 | 3.12 | 50 |
| 38 | 3.12 | 3.12 | 50 | >100 | 0.39 | 12.5 |
| 39 | 1.56 | 1.56 | 25 | >100 | 0.39 | 12.5 |
| 40 | 3.12 | 3.12 | 50 | >100 | 1.56 | 50 |
| 41 | 3.12 | 1.56 | 25 | 100 | 0.39 | 12.5 |
| 42 | 3.12 | 1.56 | 100 | 100 | 0.78 | 12.5 |
| 43 | 6.25 | 3.12 | 100 | >100 | 0.78 | 50 |
| 44 | 3.12 | 3.12 | 12.5 | >100 | 0.78 | 50 |
| 45 | 6.25 | 3.12 | 50 | >100 | 0.78 | 50 |
| 46 | 3.12 | 3.12 | 100 | 6.25 | 0.78 | 3.12 |
| 51 | 6.25 | 3.12 | 25 | >100 | 0.78 | 25 |
| 52 | 12.5 | 3.12 | 12.5 | >100 | 0.39 | 50 |
| 53 | 6.25 | 3.12 | 12.5 | 25 | 0.39 | 25 |
| 54 | 3.12 | 1.56 | 12.5 | >100 | 0.39 | 12.5 |
| 56 | 3.12 | 3.12 | 25 | 100 | 0.78 | 12.5 |
| 57 | 12.5 | 6.25 | 25 | 100 | 1.56 | 25 |
| 58 | 6.25 | 3.12 | 12.5 | >100 | 0.78 | 50 |
| 59 | 1.56 | 1.56 | 25 | 100 | 0.39 | 6.25 |
| 61 | 6.25 | 6.25 | 50 | >100 | 1.56 | 25 |
| 62 | 6.25 | 12.5 | >100 | 6.25 | 1.56 | 12.5 |
| 63 | 3.12 | 3.12 | 100 | >100 | 0.78 | 6.25 |
| 69 | 25 | 12.5 | 100 | >100 | 12.5 | >100 |
| 70 | 12.5 | 12.5 | 25 | >100 | 6.25 | 100 |
| 71 | 12.5 | 12.5 | 100 | >100 | 12.5 | 100 |
| 72 | 25 | 25 | 50 | >100 | 12.5 | >100 |
| 76 | 25 | 6.25 | 50 | >100 | 1.5 | 100 |
| 77 | 6.25 | 6.25 | 50 | 100 | 6.25 | 100 |

EXAMPLE 183

In Vivo Antibacterial Activities of 6-N'-Substituted Kanamycins

| Compound (identified by Example number) | PD₅₀ vs. E. coli (mg/kg) (subcutaneous administration) |
|---|---|
| 34 | 1.8 |
| 36 | 2.4 |
| 38 | 1.5 |
| 39 | 2.3 |
| 40 | 1.9 |
| 41 | 1.4 |
| 42 | 3.6 |
| 43 | 3.8 |
| 44 | 2.1 |
| 46 | 5.8 |
| 51 | 2.4 |
| 52 | 2.5 |
| 53 | 1.4 |
| 54 | 1.9 |
| 56 | 1.9 |
| 58 | 3.0 |
| 59 | 1.14 |
| 62 | 5.8 |
| 63 | 1.9 |
| 70 | <12.5* |

*100% protection at 12.5 mg/kg

What is claimed is:

1. A compound of formula

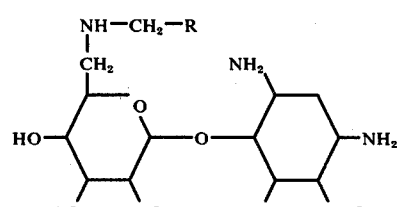

and the pharmaceutically-acceptable acid-addition salts thereof;

wherein R is selected from the group consisting of phenyl, 1-and 2-naphthyl, 1-, 2- and 9-anthryl, 1-,2-, 3-,4- and 92-,3- and 4-pyridyl, 2- and 3-furyl, 2- and 3-thienyl, 2-, 4- and 5-pyrimidyl, 2- and 3-imidazolyl, 2-, 3- and 4-quinolyl, 2- and 3-indolyl and

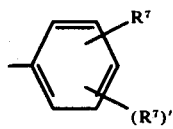

wherein R⁷ and (R⁷)' are each selected from the group consisting of fluoro, chloro, bromo, iodo, hydroxy, amino, N-(lower-alkyl) amino, N,N-di(-loweralkyl) amino, lower-alkanoylamino, nitro, lower-alkoxy, lower-alkyl, benzyloxy, trifluoromethyl, carboxy, lower-alkoxycarbonyl and phenyl;

R² is selected from the group consisting of amino and hydroxy;

R⁸ is selected from the group consisting of hydrogen and hydroxy;

and R⁵ is selected from the group consisting of hydrogen and

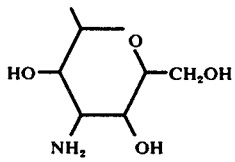

2. A compound according to claim 1, wherein R⁵ is

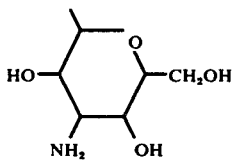

3. A compound according to claim 2, wherein R is selected from the group consisting of phenyl, naphthyl and

wherein R⁷ is selected from the group consisting of fluoro, chloro, bromo, iodo, hydroxy, amino, N-(lower-alkyl)amino, N,N-di(lower-alkyl)amino, lower-alkoxy, lower-alkyl and phenyl.

4. A compound according to claim 3, wherein R² is amino.

5. A compound according to claim 4, wherein R is selected from the group consisting of phenyl, naphthyl and 4-biphenylyl.

6. A compound according to claim 5, wherein R⁸ is hydroxy.

7. The compound according to claim 6, wherein R is phenyl.

8. The compound according to claim 6, wherein R is 1-naphthyl.

9. The compound according to claim 6, wherein R is 2-naphthyl.

10. The compound according to claim 6, wherein R is 4-biphenylyl.

11. A compound according to claim 5, wherein R⁸ is hydrogen.

12. The compound according to claim 11, wherein R is phenyl.

13. A compound according to claim 3, wherein R² and R⁸ are each hydroxy.

14. A compound according to claim 13, wherein R is

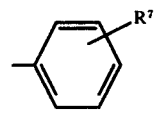

wherein R⁷ is selected from the group consisting of hydroxy, amino, N-(lower-alkyl)amino, N,N-di(lower-alkyl)amino and lower-alkoxy.

15. The compound according to claim 14, wherein R⁷ is 4-hydroxy.

16. The compound according to claim 14, wherein R⁷ is 2-hydroxy.

17. The compound according to claim 14, wherein R⁷ is 4-(N,N-dimethylamino).

18. The compound according to claim 14, wherein R⁷ is 4-amino.

19. A compound according to claim 1, wherein R² and R⁸ are each hydroxy and R⁵ is hydrogen.

20. A compound of formula:

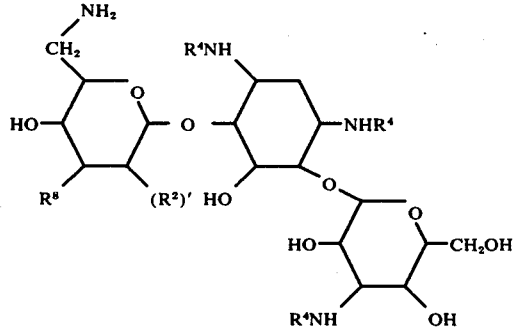

wherein R⁸ is selected from the group consisting of hydrogen and hydroxy;

(R²)' is selected from the group consisting of hydroxy and R⁴NH;

and R⁴ is selected from the group consisting of methoxycarbonyl and tertiary-butyloxycarbonyl.

21. The compound according to claim 20, wherein R⁸ and (R²)' are each hydroxy and R⁴ is methoxycarbonyl.

22. The compound according to claim 20, wherein R⁸ and (R²)' are each hydroxy and R⁴ is tertiary-butyloxycarbonyl.

23. The compound according to claim 20, wherein R⁸ is hydroxy(R²)' is R⁴NH, and R⁴ is methoxycarbonyl.

24. The compound according to claim 20, wherein R⁸ is hydroxy, (R²)' is R⁴NH, and R⁴ is tertiary-butyloxycarbonyl.

25. 5,6-O-Cyclohexylidene-2',1,3-tri(N-methoxycarbonyl)neamine.

26. 5,6-O-Cyclohexylidene-2',1,3-tri(N-tertiary-butyloxycarbonyl)-neamine.

* * * * *

UNITED STATES PATENT AND TRADEMARK OFFICE
CERTIFICATE OF CORRECTION

PATENT NO. : 4,024,332
DATED : MAY 17, 1977
INVENTOR(S) : Fenner et al

It is certified that error appears in the above-identified patent and that said Letters Patent are hereby corrected as shown below:

Col. 31, line 57 forming part of Example 92, "3,4-dimethoxyphenyl" should read -- 3-chloro-4-hydroxyphenyl --.

Col. 32, line 52 forming part of Example 147, "2-aminophenol" should read -- 2-aminophenyl --.

Col. 33, lines 53-56 and Col. 34, lines 3-6 (the headings in Example 182, following "M.I.C. (µg/ml)") which read

| Compound (identified) by Example number) | | Kleb-siella Proteus Psuedo-monas | | | | |
|---|---|---|---|---|---|---|
| | E. Coli | pneu-moniae | mira-bilis | aeru-ginosa | Staphylococcus aureus | faecalis | should read

| Compound (identified by Example number) | E. Coli | Klebsiella pneumoniae | Proteus mirabilis | Psuedomonas aeruginosa | Staphylococcus aureus | faecalis |
|---|---|---|---|---|---|---|

UNITED STATES PATENT AND TRADEMARK OFFICE
CERTIFICATE OF CORRECTION

PATENT NO. : 4,024,332
DATED : May 17, 1977
INVENTOR(S) : Fenner et al

It is certified that error appears in the above-identified patent and that said Letters Patent are hereby corrected as shown below:

Col. 34, line 18 forming part of Example 76, "1.5" should read -- 12.5 --.

Col. 34, line 65, "92-,3-" should read -- 9-phenanthryl, 2-, 3- --.

Signed and Sealed this

Thirteenth Day of December 1977

[SEAL]

Attest:

RUTH C. MASON
Attesting Officer

LUTRELLE F. PARKER
Acting Commissioner of Patents and Trademarks